(12) United States Patent
Baumann et al.

(10) Patent No.: US 8,119,617 B2
(45) Date of Patent: Feb. 21, 2012

(54) ASMASE INHIBITORS

(75) Inventors: Karl Baumann, Vienna (AT); Andreas Billich, Vienna (AT); Berndt Oberhauser, Vienna (AT)

(73) Assignee: Novartis AG, Basel (CH)

( * ) Notice: Subject to any disclaimer, the term of this patent is extended or adjusted under 35 U.S.C. 154(b) by 326 days.

(21) Appl. No.: 12/438,437

(22) PCT Filed: Aug. 21, 2007

(86) PCT No.: PCT/EP2007/007360
§ 371 (c)(1),
(2), (4) Date: Feb. 23, 2009

(87) PCT Pub. No.: WO2008/022771
PCT Pub. Date: Feb. 28, 2008

(65) Prior Publication Data
US 2010/0022482 A1 Jan. 28, 2010

(30) Foreign Application Priority Data
Aug. 23, 2006 (EP) ..................... 06119350

(51) Int. Cl.
*A61K 31/66* (2006.01)
*C07F 9/02* (2006.01)
*C07C 233/00* (2006.01)

(52) U.S. Cl. ........ 514/119; 514/114; 514/120; 558/190; 568/14; 568/15; 564/176; 564/161

(58) Field of Classification Search .................. 514/124, 514/362; 558/190; 564/176, 161; 568/14, 568/15
See application file for complete search history.

(56) References Cited

FOREIGN PATENT DOCUMENTS
JP 2000302793 A 10/2000

OTHER PUBLICATIONS

Matsui, Toshiaki et al: "Discovery of Novel Phosphonic Acid Derivatives as New Chemical Leads for Inhibitors of TNF-.alpha. production" Bioorganic & Medicinal Chemistry, 10(12).
Johnstone et al.; "Multiple physiological functions for multidrug transporter P-glycoprotein?"; TIBS—Talking Point; pp. 1-6 (2000).
Teichgraber et al., "Ceramide accumulation mediates inflammation, cell death and infection susceptibility in cystic fibrosis," Nature Medicine 14(4):382-391 (Apr. 2008).

*Primary Examiner* — Shengjun Wang
(74) *Attorney, Agent, or Firm* — Sophie Binet Cross

(57) ABSTRACT

The present invention relates to compounds of formula

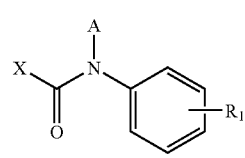

wherein the residues have various meanings and their use as pharmaceuticals.

14 Claims, No Drawings

ASMASE INHIBITORS

This application is a U.S. national Phase filing of International Serial No. PCT/EP2007/007360 filed Aug. 21, 2007, and claims priority to EP application Serial No. 06119350.4 filed Aug. 23, 2006, the contents of which are incorporated herein by reference in their entirety.

The present invention relates to mediators of acid sphingomyelinase (aSMase).

Sphingomyelinases are phosphodiesterases that catalyze the hydrolysis of sphingomyelin into ceramide and phosphorylcholine. Ceramide is a lipid second messenger in programmed cell death (apoptosis), cell differentiation and proliferation, and sphingomyelinase is a major source of ceramide in the cells. Various sphingomyelinases have been described in mammalian cells. Among those, acid sphingomyelinase (aSMase, EC 3.1.4.12) has received considerable attention, see e.g. Goni F M et al, FEBS Lett. 531:38-46 (2002); Gulbins E et al, Subcell Biochem. 36:229-44 (2002); Marchesini N et al, Biochem Cell Biol. 82:27-44 (2004); Stoffel W, Chem Phys Lipids. 102:107-21 (1999). The name of this enzyme refers to the fact that its optimum activity is at pH~5, in line with its localization in lysosomes. Deficiencies in the activity of this enzyme result in types A and B Niemann-Pick disease, an autosomal recessive lipid storage disorder accompanied by accumulation of sphingomyelin in lysosomes. Mature lysosomal aSMase is a glycoprotein with a molecular weight of 70 kDa. aSMase has been described in terms of a secretory form and an intracellular, lysosomal form, both derived from the same gene, featuring differences in their glycosylation as well as differences in N termini, see e.g. Schissel, S. L., et al, J. Biol. Chem. 273, 18250-18259, (1998). In mammalian membranes, cholesterol and sphingolipids are associated in microdomains, called rafts, separate from the bulk of glycerophospholipids. Upon stimulation of cells, these membrane rafts in resting cells are transformed into large membrane domains (called platforms) that mediate aggregation/clustering of receptor molecules; this receptor clustering is a prerequisite for reorganization of intracellular signaling molecules to transmit a signal into the cell. The generation of ceramide within rafts dramatically alters the biophysical properties of these membrane domains, since ceramide molecules have the tendency to spontaneously self-associate to small ceramide-enriched membrane microdomains. These microdomains spontaneously fuse to large ceramide-enriched platforms. Ceramide production within the cell membrane is described to be triggered by many receptors, such as CD95, CD28, TNF, CD40, FcγRII, LFA-1, TRAIL, the platelet-activating (PAF) and IL-1 receptors; as well as infection with bacteria such as *Pseudomonas aeruginosa, S. aureus, N. gonorrhoeae*, viruses such as Sindbis virus and Rhinovirus, and parasites, such as *Crytosporidium parvum*; or treatment with gamma-irradiation, UV light, or drugs, such as cisplatin and resveratrol. Ceramide release by these stimuli is catalysed by activated aSMase, see e.g. Gulbins E et at, Am J Physiol Regul Integr Comp Physiol. 2006 290:R11-26. Activation of aSMase by receptor molecules correlates with a translocation of the enzyme from intracellular stores (such as the lysosomes) onto the extracellular leaflet of the cell membrane.

Based on the essential role of aSMase in activation-induced ceramide formation as a pre-requisite for receptor stimulation, inhibitors of aSMase play a role for the treatment of conditions and diseases where ceramide formation and consequent triggering of receptors plays a pathophysiological role. Such diseases encompass autoimmune diseases, such as multiple sclerosis and arthritis; septic shock; lung emphysema and chronic obstructive pulmonary disease (COPD); cystic fibrosis; diseases where abnormal apoptosis play a role, such as neuronal degeneration, in particular stroke and Alzheimer's disease, and myocardial infarction; tumor growth, in particular the growth of melanoma. Furthermore, inhibitors of aSMase have been proposed according to findings to be useful for the treatment and prevention of diseases caused by infectious pathogens, such as viruses, bacteria and parasites.

In particular, a role of aSMase in septic shock has been documented. Interestingly, a compound, designated NB6, which induces proteolytic cleavage of aSMase, was shown to protect mice from lethal LPS-shock, see e.g. Claus R A et al, FASEB J. 19:1719-21 (2005). Furthermore, a role of aSMase in atherosclerosis has been demonstrated, see e.g. Tabas I., Chem Phys Lipids. 1999 102(1-2):123-30. This is based on the observation that cleavage of sphingomyelin by associated with low-density lipoprotein (LDL) triggers subendothelial aggregation of LDL as an important step in foam cell formation, a critical pathophysiological effect in atherosclerosis. Therefore, aSMase inhibitors are shown to be useful in the prevention and treatment of atherosclerosis.

It has been shown that aSMase is elevated in patients with mental depression, see e.g. Kornhuber J et al, J Neural Transm. 112:1583-90 (2005). Tricylic antidepressants, in particular imipramine, are drugs used in the treatment of mental depression. This class of compounds also induces proteolytic degradation of aSMase, leading to overall inhibition of cellular aSMase activity. Therefore, inhibitors of aSMase are shown to be useful in the treatment of depressive disorders, such as major depression.

Now surprisingly compounds have been found which inhibit the action of aSMase.

In one aspect the present invention provides a compound of formula

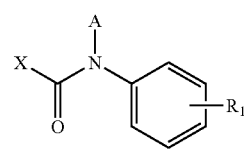

wherein
A is hydrogen or $(C_{1-4})$alkyl,
$R_1$ is a group Y—$R_2$,
Y is not present or is $(C_{1-4})$alkylene, which alkylene optionally is substituted, e.g. one or morefold, by halogen, such as F,
$R_2$ is —P(O)(OH)(OH), or a group of formula

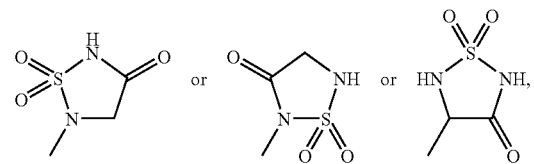

X is a group of formula

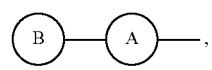

ring A is $(C_{5-12})$cycloalkylene, $(C_{5-12})$cycloalkenylene or phenylene, and ring B is unsubstituted or substituted $(C_{5-12})$cycloalkyl, $(C_{5-12})$cycloalkenyl or $(C_{6-12})$aryl, e.g. unsubstituted, or, e.g. one or morefold, substituted by $R_5$, wherein $R_5$ is halogen, halo$(C_{1-4})$alkyl, halo$(C_{1-4})$alkyloxy, carboxyl, nitro, amino, a phosphor containing group, a sulfur containing group, acyl or acyloxy comprising 1 to 12 carbon atoms beside the CO group, or $R_5$ is a group —$ZR_6$, wherein Z is not present or is NH, O or S and $R_6$ is hydrogen if Z is present, or $R_6$ is, e.g. whether Z is present, or not, $(C_{3-12})$cycloalkyl, $(C_{5-12})$cycloalkenyl, $(C_{6-12})$aryl, or heterocyclyl, including aromatic and aliphatic heterocyclyl comprising 3 to 12 ring members, e.g. 5 or 6, and 1 to 4 heteroatoms selected from N, O or S, or $(C_{1-22})$alkyl, such as $(C_{1-12})$alkyl, $(C_{2-22})$alkenyl, such as $(C_{2-12})$alkenyl, or $(C_{2-22})$alkynyl, such as $C_{2-12})$alkynyl, which alkyl, alkenyl or alkynyl is unsubstituted or substituted by $(C_{6-12})$aryl, such as phenyl, or a prodrug of a compound of formula I which is a compound of formula I wherein $R_2$ is a phosphoric acid ester or phosphoric acid amide (amidate) group, e.g. in salt form, wherein the phosphoric acid ester or amide (amidate) moiety is a group which is hydrolysable, e.g. hydrolysable in vivo, or a prodrug of a compound of formula I which is a compound of formula I wherein the nitrogen of the amide group is substituted by a group which is hydrolysable e.g. hydrolysable in vivo, e.g. such hydrolysable group is prone to be split off in vivo.

In another aspect the present invention provides a compound of formula I, wherein A is hydrogen and the other residues are as defined above or below.

In another aspect the present invention provides a compound of formula I, wherein A is $(C_{1-4})$alkyl, such as methyl or ethyl, and the other residues are as defined above or below.

In a compound of formula I preferably $R_1$ is a group Y—$R_2$ and Y is not present; or $R_1$ is a group Y—$R_2$ and Y is $(C_{1-4})$alkylene, e.g. methylene; or $R_1$ is a group Y—$R_2$ and Y is alkylene substituted, e.g. one or morefold, by halogen, such as F, e.g. difluoromethylene, tetrafluoroethylene.

In a compound of formula I preferably $R_1$ is in ortho position of the phenyl ring to which it is attached, or $R_1$ is in meta position of the phenyl ring to which it is attached, or $R_1$ is in para position of the phenyl ring to which it is attached.

In a compound of formula I preferably $R_2$ is —P(O)(OH)(OH); or $R_2$ is a group of formula

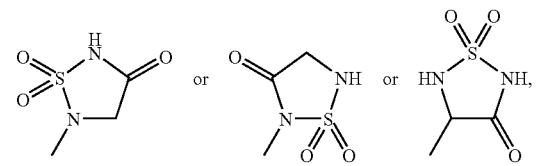

or such as a group of formula

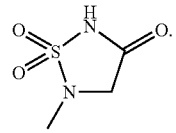

In a compound of formula I preferably ring A is unsubstituted phenylene, or ring A is unsubstituted $(C_{5-12})$cycloalkylene or $(C_{5-12})$cyclalkenylene, such as adamantylene.

In a compound of formula I preferably ring B is $(C_{6-12})$aryl, such as phenyl which aryl is unsubstituted or substituted by $R_5$, wherein $R_5$ is as defined above, or ring B is unsubstituted $(C_{5-12})$cycloalkyl or $(C_{5-12})$cycloalkenyl, or $(C_{5-12})$cycloalkyl or $(C_{5-12})$cycloalkenyl substituted by $R_5$, wherein $R_5$ is as defined above.

In a compound of formula I preferably if ring B is substituted phenyl, phenyl is substituted in position 4.

In a compound of formula I preferably if present, $R_5$ is a group —$ZR_6$, wherein Z is not present or is NH, O or S, preferably Z is not present or is O, and $R_6$ is hydrogen in case that Z is present, or $R_6$, whether Z is present or not, is alkyl, alkenyl or alkynyl, wherein alkyl comprises 1 to 22, such as 1 to 12 carbon atoms, and alkenyl or alkynyl comprise 2 to 22, such as 2 to 12 carbon atoms, preferably alkyl, wherein alkyl, alkenyl or alkynyl are unsubstituted or substituted by $(C_{6-12})$aryl, such as phenyl.

In a compound of formula I more preferably $R_5$ is hydroxy, alkyl or alkoxy wherein "alk" comprises 1 to 22, such as 1 to 12 carbon atoms, which alkyl or alkoxy optionally is substituted by phenyl.

If in a compound of formula I A is $(C_{1-4})$alkyl, such as methyl or ethyl, ring B preferably is phenyl substituted by $R_5$, $R_5$ is a group —$ZR_6$, wherein Z is is NH, O or S and $R_6$ is $(C_{1-22})$alkyl, such as $(C_{1-12})$alkyl, $(C_{2-22})$alkenyl, such as $(C_{2-12})$alkenyl, or $(C_{2-22})$alkynyl, such as $C_{2-12})$alkynyl, which alkyl, alkenyl or alkynyl is unsubstituted or substituted by $(C_{6-12})$aryl, such as phenyl; more preferably ring B is phenyl substituted by $R_5$, $R_5$ is a group —$ZR_6$, wherein Z is is NH, O or S, preferably O, and $R_6$ is $(C_{1-22})$alkyl.

In another aspect the present invention provides a compound of formula I, wherein A is hydrogen, methyl or ethyl, $R_1$ is a group Y—$R_2$, Y is not present or is —$CH_2$—, —$CF_2$— or —$CF_2$—$CF_2$—, $R_2$ is —P(O)(OH)(OH); or $R_2$ is a group of formula

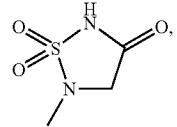

X is a group of formula

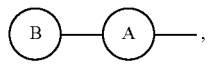

ring A is unsubstituted phenylene or adamantylene, and
ring B is phenyl, which phenyl is unsubstituted or substituted by hexyl, hydroxy, methoxy, butoxy, e.g. n-butoxy, heptyloxy, octyloxy, decyloxy or benzyloxy.

In another aspect the present invention provides a prodrug of a compound of formula I.

A prodrug of a compound of formula I is preferably
a compound of formula I wherein $R_2$ is a phosphoric acid ester or amide (amidate) group,
e.g. in salt form, wherein the phosphoric acid ester or amide (amidate) moiety is a group which is hydrolysable, e.g. hydrolysable in vivo and the other residues are as defined above or below, or
a compound of formula I wherein A is other than $(C_{1-4})$alkyl, e.g. the nitrogen of the amide group is substituted by a group which is hydrolysable e.g. hydrolysable in vivo, such as a compound of formula

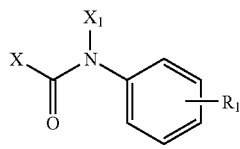

I' wherein $X_1$ is a group of formula

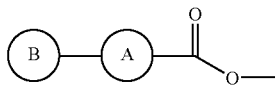

wherein ring A and ring B are as defined above, or
a compound of formula I wherein $R_2$ is a phosphoric acid ester or amide (amidate) group,
e.g. in salt form, wherein the phosphoric acid ester or amide (amidate) moiety is a group which is hydrolysable, e.g. hydrolysable in vivo and the other residues are as defined above or below and wherein A is other than $(C_{1-4})$alkyl, e.g. the nitrogen of the amide group is substituted by a group which is hydrolysable e.g. hydrolysable in vivo, such as a compound of formula

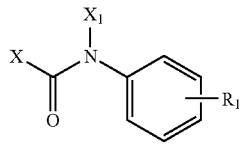

I' wherein $X_1$ is a group of formula

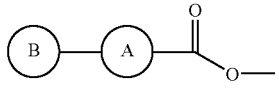

wherein ring A and ring B are as defined above.

In one preferred embodiment a prodrug of a compound of formula I preferably is a compound of formula I, wherein $R_1$ is a group —Y—$R_2$', wherein
$R'_2$ is —P(O)(OR$_3$)(OR$_4$), —P(O)(NHR$_3$)(NHR$_4$) or —P(O)(NHR$_3$)(OR$_4$), more preferably —P(O)(OR$_3$)(OR$_4$), wherein $R_3$ and $R_4$ independently of each other are hydrogen or $(C_{1-4})$alkyl and wherein at least one of $R_3$ and $R_4$ is $(C_{1-4})$alkyl, or
$R'_2$ is —P(O)(OR'$_3$)(OR'$_4$), —P(O)(NHR'$_3$)(NHR'$_4$) or —P(O)(NHR'$_3$)(OR'$_4$), more preferably —P(O)(OR'$_3$)(OR'$_4$), wherein R'$_3$ and R'$_4$ independently of each other are hydrogen or $(C_{1-4})$alkyl, wherein alkyl is substituted by $(C_{1-6})$alkylcarbonyloxy, such as tert-butylcarbonyloxy, and wherein at least one of R'$_3$ and R'$_4$ is other than hydrogen: or
$R'_2$ is —P(O$^-$)(O)(O—CH$_2$—CH$_2$—N$^+$(C(CH$_3$)$_3$);

In another preferred embodiment a prodrug of a compound of formula I preferably is a compound of formula I wherein A is other than $(C_{1-4})$alkyl, e.g. the nitrogen of the amide group is substituted by a group which is hydrolysable e.g. hydrolysable in vivo, such as a compound of formula

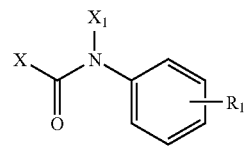

I' wherein $X_1$ is a group of formula

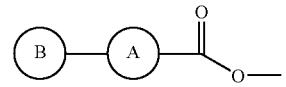

wherein ring A and ring B are as defined above.

In another aspect the present invention provides a prodrug of a compound of formula I which is a compound of formula

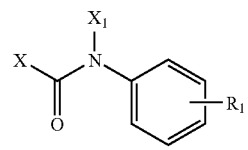

I' wherein $R_1$ is a group Y—$R_2$ or —Y—$R_2$',
Y is not present or is —CH$_2$—, —CF$_2$— or —CF$_2$—CF$_2$—,
$R_2$ is —P(O)(OH)(OH); or
$R_2$ is a group of formula

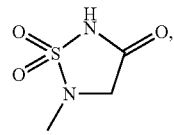

$R'_2$ is —P(O)(OR$_3$)(OR$_4$) wherein $R_3$ and $R_4$ independently of each other are hydrogen or $(C_{1-4})$alkyl and wherein at least one of $R_3$ and $R_4$ is $(C_{1-4})$alkyl, or R'$_2$ is —P(O)(OR'$_3$)(OR'$_4$) wherein R'$_3$ and R'$_4$ independently of each other are hydrogen or (C$_{1-4}$)alkyl, wherein alkyl is substituted by (C$_{1-6}$)alkylcarbonyloxy and wherein at least one of R'$_3$ and R'$_4$ is other than hydrogen; or R'$_2$ is —P(O$^-$)(O)(O—CH$_2$—CH$_2$—N$^+$(C(CH$_3$)$_3$).

X is a group of formula

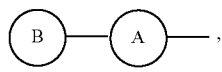

ring A is unsubstituted phenylene or adamantylene, and
ring B is phenyl, which phenyl is unsubstituted or substituted by hexyl, decyl, hydroxy, methoxy, butoxy, e.g. n-butoxy, heptyloxy, octyloxy, decyloxy or benzyloxy, and
X$_1$ is hydrogen or a group of formula

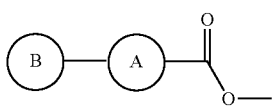

wherein ring A and ring B are as defined above,
with the proviso that
either X$_1$ is other than hydrogen, or R$_1$ is —Y—R$_2$', or
X$_1$ is other than hydrogen and R$_1$ is —Y—R$_2$',
and with the proviso that, if R$_2$ is a group of formula

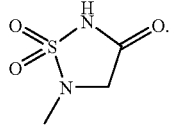

then R$_1$ is —Y—R$_2$'.

In a compound of formula I each single group of substituents defined, or each single substituent defined, respectively, may be a preferred group of substituents, or substituent, respectively, e.g. independently of each other group of substituents or substituent defined.

In another aspect the present invention provides a compound of formula I, selected from the group consisting of
1. 4'-Octyloxy-biphenyl-4-carboxylic acid [3-(1,1,4-trioxo-1lambda*6*-[1,2,5]thiadiazolidin-2-yl)-phenyl]-amide,
2. {2-[(4'-Octyloxy-biphenyl-4-carbonyl)-amino]-benzyl}-phosphonic acid,
3. {2-[(4'-Hexyl-biphenyl-4-carbonyl)-amino]-benzyl}-phosphonic acid,
4. {2-[(3-Phenyl-adamantane-1-carbonyl)-amino]-benzyl}-phosphonic acid,
5. {2-[(4'-Methoxy-biphenyl-4-carbonyl)-amino]-benzyl}-phosphonic acid,
6. (Difluoro-{2-[(4'-octyloxy-biphenyl-4-carbonyl)-amino]-phenyl}-methyl)-phosphonic acid,
7. (Difluoro-{3-[(4'-octyloxy-biphenyl-4-carbonyl)-amino]-phenyl}-methyl)-phosphonic acid,
8. (Difluoro-{4-[(4'-octyloxy-biphenyl-4-carbonyl)-amino]-phenyl}-methyl)-phosphonic acid,
9. (Difluoro-{2-[(4'-octyloxy-biphenyl-4-carbonyl)-amino]-phenyl}-methyl)-phosphonic acid diethyl ester,
10. (Difluoro-{3-[(4'-octyloxy-biphenyl-4-carbonyl)-amino]-phenyl}-methyl)-phosphonic acid diethyl ester,
11. (Difluoro-{4-[(4'-octyloxy-biphenyl-4-carbonyl)-amino]-phenyl}-methyl)-phosphonic acid diethyl ester,
12. (Difluoro-{2-[(4'-octyloxy-biphenyl-4-carbonyl)-amino]-phenyl}-methyl)-phosphonic acid monoethyl ester,
13. (Difluoro-{3-[(4'-octyloxy-biphenyl-4-carbonyl)-amino]-phenyl}-methyl)-phosphonic acid monoethyl ester,
14. (Difluoro-{4-[(4'-octyloxy-biphenyl-4-carbonyl)-amino]-phenyl}-methyl)-phosphonic acid monoethyl ester,
15. (1,1,2,2-Tetrafluoro-2-{4-[(4'-octyloxy-biphenyl-4-carbonyl)-amino]-phenyl}-ethyl)-phosphonic acid diethyl ester,
16. (1,1,2,2-Tetrafluoro-2-{4-[(4'-octyloxy-biphenyl-4-carbonyl)-amino]-phenyl}-ethyl)-phosphonic acid monoethyl ester,
17. (1,1,2,2-Tetrafluoro-2-{4-[(4'-octyloxy-biphenyl-4-carbonyl)-amino]-phenyl}-ethyl)-phosphonic acid,
18. {2-[(4'-Octyloxy-biphenyl-4-carbonyl)-amino]-phenyl}-phosphonic acid,
19. {2-[(4'-Octyloxy-biphenyl-4-carbonyl)-amino]-phenyl}-phosphonic acid monoethyl ester,
20. {2-[(4'-Octyloxy-biphenyl-4-carbonyl)-amino]-phenyl}-phosphonic acid diethyl ester,
21. {3-[(4'-Octyloxy-biphenyl-4-carbonyl)-amino]-phenyl}-phosphonic acid,
22. {3-[(4'-Octyloxy-biphenyl-4-carbonyl)-amino]-phenyl}-phosphonic acid monoethyl ester,
23. {3-[(4'-Octyloxy-biphenyl-4-carbonyl)-amino]-phenyl}-phosphonic acid diethyl ester,
24. [3-(4-Heptyloxy-benzoylamino)-phenyl]-phosphonic acid,
25. {4-[(4'-Octyloxy-biphenyl-4-carbonyl)-amino]-phenyl}-phosphonic acid monoethyl ester,
26. {4-[(4'-Octyloxy-biphenyl-4-carbonyl)-amino]-phenyl}-phosphonic acid diethyl ester,
27. 3-[(4'-Octyloxy-biphenyl-4-carbonyl)-amino]-benzyl}-phosphonic acid,
28. {3-[(4'-Octyloxy-biphenyl-4-carbonyl)-amino]-benzyl}-phosphonic acid monoethyl ester,
29. {2-[(4'-Decyloxy-biphenyl-4-carbonyl)-amino]-benzyl}-phosphonic acid diethyl ester,
30. {2-[(4'-Decyloxy-biphenyl-4-carbonyl)-amino]-benzyl}-phosphonic acid,
31. {2-[(4'-Benzyloxy-biphenyl-4-carbonyl)-amino]-benzyl}-phosphonic acid,
32. {2-[(4'-Hydroxy-biphenyl-4-carbonyl)-amino]-benzyl}-phosphonic acid,
33. {4-[(4'-Octyloxy-biphenyl-4-carbonyl)-amino]-benzyl}-phosphonic acid,
34. {2-[(Biphenyl-4-carbonyl)-amino]-benzyl}-phosphonic acid,
35. {2-[(4'-Butoxy-biphenyl-4-carbonyl)-amino]-benzyl}-phosphonic acid,
36. [2-({2-[(4'-Hexyl-biphenyl-4-carbonyl)-amino]-benzyl}-hydroxy-phosphinoyloxy)-ethyl]-trimethyl-ammonium,
37. (Difluoro-{2-[(4'-octyloxy-biphenyl-4-carbonyl)-amino]-phenyl}-methyl)-phosphonic acid ethyl ester methyl ester,
38. (1,1,2,2,2-Tetrafluoro-2-{4-[(4'-octyloxy-biphenyl-4-carbonyl)-(4'-octyloxy-biphenyl-4-carbonyloxy)-amino]-phenyl}-ethyl)-phosphonic acid diethyl ester,
39. 2,2-Dimethyl-propionic acid hydroxy-{2-[(4'-octyloxy-biphenyl-4-carbonyl)-amino]-benzyl}-phosphinoyloxymethyl ester, 40. 2,2-Dimethyl-propionic acid (2,2-dimethyl-propionyloxymethoxy)-{2-[(4'-octyloxy-biphenyl-4-carbonyl)-amino]-benzyl}-phosphinoyloxymethyl ester,
41. (Difluoro-{4-[(4'-octyloxy-biphenyl-4-carbonyl)-(4'-octyloxy-biphenyl-4-carbonyloxy)-amino]-phenyl}-methyl)-phosphonic acid diethyl ester,
42. (1,1,1,2,2-Tetrafluoro-2-{2-[(4'-octyloxy-biphenyl-4-carbonyl)-amino]-phenyl}-ethyl)-phosphonic acid diethyl ester,
43. (1,1,2,2-Tetrafluoro-2-{3-[(4'-octyloxy-biphenyl-4-carbonyl)-amino]-phenyl}-ethyl)-phosphonic acid diethyl ester,
44. (Difluoro-{4-[4'-octyloxy-biphenyl-4-carbonyl)-(4'-octyloxy-biphenyl-4-carbonyloxy)-amino]-phenyl}-methyl)-phosphonic acid,
45. (1,1,2,2-Tetrafluoro-2-{3-[(4'-octyloxy-biphenyl-4-carbonyl)-amino]-phenyl}-ethyl)-phosphonic acid,
46. (1,1,2,2-Tetrafluoro-2-{2-[(4'-octyloxy-biphenyl-4-carbonyl)-amino]-phenyl}-ethyl)-phosphonic acid
47. (2-{2-[(4'-Octyloxy-biphenyl-4-carbonyl)-amino]-phenyl}-ethyl)-phosphonic acid diethyl ester,
48. (2-{3-[(4'-Octyloxy-biphenyl-4-carbonyl)-amino]-phenyl}-ethyl)-phosphonic acid diethyl ester,
48a. (2-{4-[(4'-Octyloxy-biphenyl-4-carbonyl)-amino]-phenyl}-ethyl)-phosphonic acid diethyl ester,
49. (2-{2-[(4'-Octyloxy-biphenyl-4-carbonyl)-amino]-phenyl}-ethyl)-phosphonic acid,
50. (2-{3-[(4'-Octyloxy-biphenyl-4-carbonyl)-amino]-phenyl}-ethyl)-phosphonic acid,
51. (2-{4-[(4'-Octyloxy-biphenyl-4-carbonyl)-amino]-phenyl}-ethyl)-phosphonic acid,
52. {4-[(4'-Octyloxy-biphenyl-4-carbonyl)-amino]-phenyl}-phosphonic acid,
53. {3-[(4'-Octyloxy-biphenyl-4-carbonyl)-amino]-benzyl}-phosphonic acid diethyl ester.
54. ({2-[Ethyl-(4-octyloxy-biphenyl-4-carbonyl)-amino]-phenyl}-difluoro-methyl)-phosphonic acid diethyl ester,
55. (Difluoro-{2-[methyl-(4'-octyloxy-biphenyl-4-carbonyl)-amino]-phenyl}-methyl)-phosphonic acid diethyl ester,
56. (Difluoro-{2-[methyl-(4'-octyloxy-biphenyl-4-carbonyl)-amino]-phenyl}-methyl)-phosphonic acid ethyl ester methyl ester,
57. (Difluoro-{4-[methyl-(4'-octyloxy-biphenyl-4-carbonyl)-amino]-phenyl}-methyl)-phosphonic acid diethyl ester,
58. (Difluoro-{4-[methyl-(4'-octyloxy-biphenyl-4-carbonyl)-amino]-phenyl}-methyl)-phosphonic acid ethyl ester methyl ester,
59. (Difluoro-{3-[methyl-(4'-octyloxy-biphenyl-4-carbonyl)-amino]-phenyl}-methyl)-phosphonic acid diethyl ester,
60. (Difluoro-{3-[methyl-(4'-octyloxy-biphenyl-4-carbonyl)-amino]-phenyl}-methyl)-phosphonic acid ethyl ester methyl ester,
61. (Difluoro-{3-[methyl-(4'-octyloxy-biphenyl-4-carbonyl)-amino]-phenyl}-methyl)-phosphonic acid monoethyl ester,
62. (Difluoro-{4-[methyl-(4'-octyloxy-biphenyl-4-carbonyl)-amino]-phenyl}-methyl)-phosphonic acid,
63. (Difluoro-{2-[methyl-(4'-octyloxy-biphenyl-4-carbonyl)-amino]-phenyl}-methyl)-phosphonic acid, and
64. (Difluoro-{3-[methyl-(4'-octyloxy-biphenyl-4-carbonyl)-amino]-phenyl}-methyl)-phosphonic acid;
e.g. such as compounds of formula I' or of formula I as indicated in the Examples 1 to 62 in TABLE 1 and TABLE 2 below in the examples part.

Compounds provided by the present invention are hereinafter designated as "compound(s) of (according to) the present invention". A compound of the present invention includes a compound in any form, e.g. in free form, in the form of a salt, in the form of a solvate and in the form of a salt and a solvate.

In another aspect the present invention provides a compound of the present invention in the form of a salt.

Such salts include preferably pharmaceutically acceptable salts, although pharmaceutically unacceptable salts are included, e.g. for preparation/isolation/purification purposes. A compound of the present invention in free form may be converted into a corresponding compound in the form of a salt; and vice versa. A compound of the present invention in free form or in the form of a salt and in the form of a solvate may be converted into a corresponding compound in free form or in the form of a salt in non-solvated form; and vice versa.

A compound of the present invention may exist in the form of isomers and mixtures thereof; e.g. optical isomers, diastereoisomers, cis/trans conformers. A compound of the present invention may e.g. contain asymmetric carbon atoms or phosphorous atoms and may thus exist in the form of enatiomers or diastereoisomers and mixtures thereof, e.g. racemates. A compound of the present invention may be present in the (R)-, (S)- or (R,S)-configuration preferably in the (R)- or (S)-configuration regarding specified positions in the compound of the present invention.

Isomeric mixtures may be separated as appropriate, e.g. according, e.g. analogously, to a method as conventional, to obtain pure isomers. The present invention includes a compound of the present invention in any isomeric form and in any isomeric mixture.

The present invention also includes tautomers of a compound of the present invention, where tautomers can exist.

In another aspect the present invention provides a process for the production of a compound of formula I, or a prodrug thereof as defined above, comprising the steps
i) reacting a compound of formula

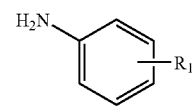

II with a compound of formula

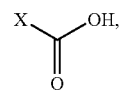

III such as a compound of formula

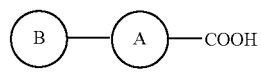

III' wherein X and $R_1$, e.g. and ring A and ring B, are as defined above, and wherein functional groups optionally are protected, in organic solvent, e.g. polar organic solvent, such as DMF, e.g. in the presence of coupling agent, such as N-ethyl, N'-(3-dimethylaminopropyl)-carbodiimide, 1-hydroxy-7-aza-1,2,3-benzotriazole) and a base, e.g. an amine, such as a tertiary amine, e.g. diisopropylethyl amine, ii) optionally removing protecting groups,
iii) isolating a compound of formula I or prodrug thereof, wherein X and $R_1$ are as defined above from the reaction mixture, and
iv) optionally further reacting to obtain another compound of formula I or prodrug thereof, e.g. alkylating the amine group with a $(C_{1-4})$alkylhalogenide, such as a $(C_{1-4})$alkyliodide in the presence of lithium hexamethyldisilazide (LiHMDS), to obtain a compound of formula I, or prodrug thereof wherein A is $(C_{1-4})$alkyl, e.g. before or after step ii).

In an intermediate of formula II, or of formula III (starting materials), functional groups, if present, optionally may be in protected form or in the form of a salt, if a salt-forming group is present. Protecting groups, optionally present, may be removed at an appropriate stage, e.g. according, e.g. analogously, to a method as conventional. E.g., if a compound of formula II comprises a phosphonic acid group, the phosphonic acid group in a compound of formla II may be in the form of a phosphonic acid alkylester group. The alkoxy groups may be removed, e.g. in step ii), e.g. by treatment with a trialkylsilyl iodide, such as trimethylsilyl iodide, in organic solvent, e.g. polar organic solvent, e.g. a halogenated carbohydrate, such as $CH_2Cl_2$.

A compound of the present invention thus obtained may be converted into another compound of the present invention, e.g. a compound of the present invention obtained in free form may be converted into a salt of a compound of the present invention and vice versa.

The above reaction is an amine acylation reaction and may be carried out as appropriate, e.g. according, e.g. analaogously to amine acylation reactions as carried out in organic chemistry.

Intermediates (starting materials) of formula II or of formula III (III') are known or may be prepared according, e.g. analogously, to a method as conventional or as specified herein.

For example, a compound of formula II, wherein $R_1$ is —Y—P(O)(OH)(OH) e.g. in esterfied form, e.g. in the form of the —$PO_3H_2$ diethylester, namely —$CH_2$—P(O)($OC_2H_5$)$_2$, may be e.g. obtained by reduction of the nitro group in a compound of formula

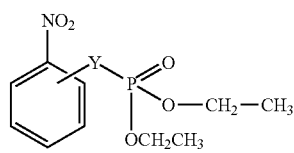

IV e.g. by hydrogenation in the presence of Pd—C as a catalyst, in organic solvent, e.g. polar organic solvent, such as an alcohol, e.g. ethanol, and isolating a compound of formula II, wherein the phosphonic acid group is in a protected form from the reaction mixture. A compound of formula IV may be e.g. obtained by reacting a compound of formula

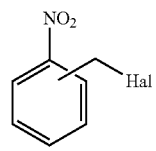

V wherein Hal is halogen, e.g. Br or I, with triethylphosphite in organic solvent, such as apolar organic solvent, e.g. toluene, and isolating a compound of formula IV obtained from the reaction mixture.

For example, a compound of formula II, wherein $R_1$ is —$CF_2$—P(O)($OC_2H_5$)$_2$ or —$CF_2CF_2$—P(O)($OC_2H_5$)$_2$ may be obtained by reacting a compound of formula

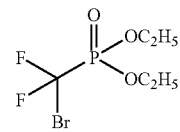

with zinc in the presence of catalytic amounts of trimethylchlorosilane in organic solvent, e.g. polar organic solvent, such as N,N-dimethylformamide, to obtain a compound of formula

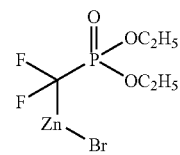

which compound is further reacted in the presence of Cu(I)Br with a compound of formula

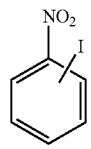

to obtain a mixture of compounds of formula

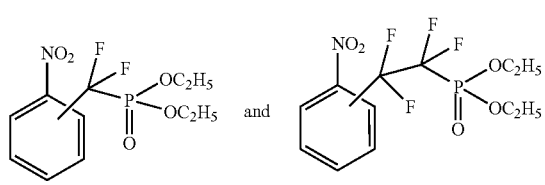

separating that mixture, e.g. by chromatography, and hydrogenating the separated compound obtained in the presence of Pd—C as a catalyst, in organic solvent, e.g. polar organic solvent, such as an alcohol, e.g. ethanol, and isolating a compound of formula II, wherein $R_1$ is —$CF_2$—P(O)($OC_2H_5$)$_2$, or —$CF_2$—$CF_2$—P(O)($OC_2H_5$)$_2$, respectively.

For example, a compound of formula II, wherein $R_2$ is a group of formula

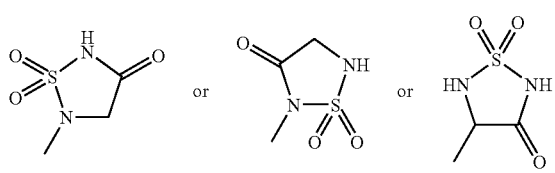

such as a group of formula

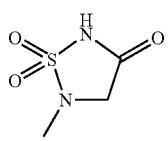

may be obtained by reduction of the nitro group in a compound of formula

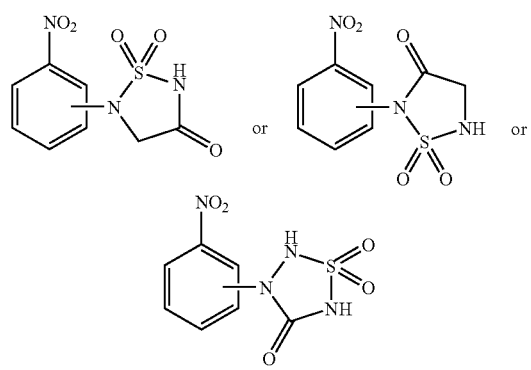

e.g.

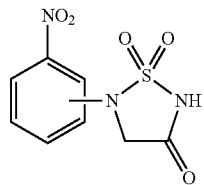

e.g. by hydrogenation in the presence of Pd—C as a catalyst, in organic solvent, e.g. polar organic solvent, such as an alcohol, e.g. methanol, and isolating a compound of formula II from the reaction mixture.

A compound of formula VI may be e.g. obtained by ring closure of the residue attached to the nitrobenzene of formula

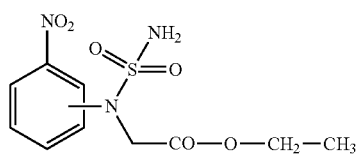

e.g. in organic solvent, e.g. polar organic solvent, such as tetrahydrofurane, in the presence of $NaN[Si(CH_3)_3]_2$.

A compound of formula VII may be e.g. obtained by removing the tert-butoxycarbonyl (BOC) group in a compound of formula

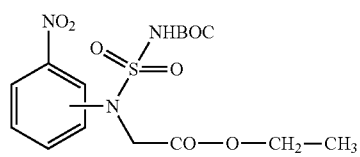

e.g. by treatment with diluted trifluoroacetic acid in anorganic solvent, such as $H_2O$.

A compound of formula VIII may be e.g. obtained by reacting the amine group in a compound of formula

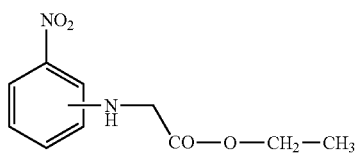

with the reaction product of $ClSO_2NCO$ and tert-butanol, in organic solvent, e.g. apolar organic solvent, such as an halogenated carbohydrate, e.g. $CH_2Cl_2$, in the presence of a tertiary amine, e.g. triethylamine and isolating a compound of formula VIII obtained from the reaction mixture.

Any compound described herein, e.g. a compound of the present invention and intermediates of formula II, III, III', IV, V, VI, VII, VIII and IX, may be prepared as appropriate, e.g. according, e.g. analogously, to a method as conventional, e.g. or as specified herein.

Intermediates in the production of a compound of the present invention are herein also designated as an intermediate of (according to) the present invention. Intermediates of the present invention are partially and such novel intermediates also form part of the present invention.

In another aspect the present invention provides a compound, such as an intermediate of the present invention, which is selected from the group consisting of [1,1,2,2-Tetrafluoro-2-(2-nitro-phenyl)-ethyl]-phosphonic acid diethyl ester, such as of formula

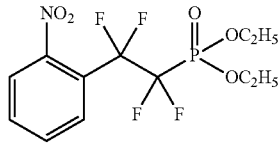

[Difluoro-(3-nitro-phenyl)-methyl]-phosphonic acid diethyl ester, such as of formula

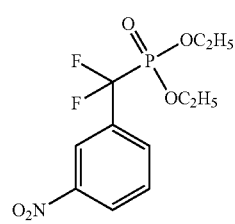

[1,1,2,2-Tetrafluoro-2-(3-nitro-phenyl)-ethyl]-phosphonic acid diethyl ester, such as of formula

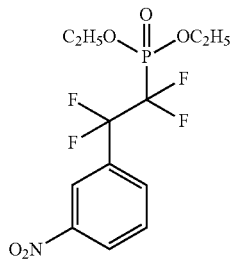

[1,1,2,2-Tetrafluoro-2-(4-nitro-phenyl)-ethyl]-phosphonic acid diethyl ester, such as of formula

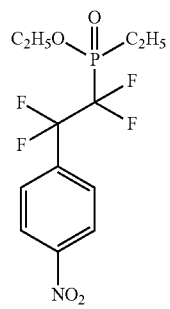

[(2-Ethylamino-phenyl)-difluoro-methyl]-phosphonic acid diethyl ester,
[Difluoro-(2-hydroxyamino-phenyl)-methyl]-phosphonic acid diethyl ester,
[(3-Ethylamino-phenyl)-difluoro-methyl]-phosphonic acid diethyl ester, and
(3-nitro-phenylethynyl)-phosphonic acid diethyl ester;
e.g. which intermediate is useful for preparing a compound of the present invention.

The compounds of the present invention, e.g. including a compound of formula I, exhibit pharmacological activity and are therefore useful as pharmaceuticals. E.g., the compounds of the present invention have been found to inhibit sphingomyelinase (aSMase) activity.

Sphingomyelinase (aSMase) activity e.g. may be determined according to the following Sphingomyelinase (aSMase) TEST ASSAY:

Sphingomyelinase (aSMase) TEST ASSAY

The activity of the compounds as inhibitors of acid sphingomyelinase (aSMase) is determined according to the following protocol:
Recombinant human aSMase (EC 3.1.4.12) is purified from the supernatants of transfected HEKfreestyle 293 cells.
The enzyme substrate Bodipy-C12 sphingomyelin (purchased from MolecularProbes) is dissolved in DMSO at a concentration of 1 mM. One volume of this stock solution is mixed with 9 volumes of 0.5% Triton X-100 in water. This mixture is subjected to sonication for 10 min to yield a micellar preparation of the substrate.
The inhibitor is dissolved in DMSO at graded concentrations.
The reaction mixture is set up by mixing 27.5 µl of buffer (250 mM sodium acetate, pH 5, containing 1 mM EDTA) with 10 µl of substrate solution (to yield 20 µM final concentration of substrate) and 2.5 µl of inhibitor dilutions or DMSO as uninhibited control.
The reaction is started by addition of 10 µl of enzyme solution (to make a final concentration of 25 nM).
The reaction is allowed to proceed for 1 hour at 37° C.
The reaction is stopped by addition of 125 µl isopropanol/heptane/5 M sulfuric acid (40:10:1).
75 µl heptane and 67 µl water are added. Samples are mixed and briefly centrifuged to separate layers.
From the upper layer of the extracted samples, 4 µl are removed and transferred into 200 µl isopropanol contained in the wells of white 96-well plates.
Fluorescence is measured in a Spectramax plate reader (Molecular Devices) against isopropanol as a blank with excitation at 485 nm and emission at 538 nm.
By comparing the fluorescence units in the uninhibited control samples vs. the samples containing inhibitor at graded concentrations, the concentration inhibiting the enzyme by 50% ($IC_{50}$) is determined.

In the Sphingomyelinase (aSMase) TEST ASSAY compounds of the present invention show $IC_{50}$ values in the nanomelucar up to the low micromolar range.

The compounds of the present invention show activity in that Sphingomyelinase (aSMase) TEST ASSAY and are therefore indicated for the treatment of disorders (diseases) mediated by sphingomyelinase (aSMase) activity.

Disorders, e.g. including diseases, mediated by sphingomyelinase (aSMase) activity and which are prone to be successfully treated with an inhibitor of sphingomyelinase (aSMase) activity, e.g. with compounds of the present invention, include disorders, wherein the activity of sphingomyelinase (aSMase) play a causal or contributory role.

Such disorders are preferably
septic shock,
autoimmune diseases, including multiple sclerosis and arthritis,
lung emphysema and chronic obstructive pulmonary disease (COPD),
cystic fibrosis,
atherosclerosis,
neuronal degeneration, in particular stroke and Alzheimer's disease,
mental depression,
infectious diseases caused by pathogens, such as viruses, bacteria and parasites
tumor growth, in particular growth of melanomas.

Disorders mediated by sphingomyelinase (aSMase) are expected to include e.g.
disorders associated with conditions of the immune system,
immune, such as autoimmune disorders e.g. including Graves' disease, Hashimoto's disease (chronic thyroiditis), multiple sclerosis, rheumatoid arthritis, arthritis, gout, osteoarthritis, scleroderma, lupus syndromes, systemic lupus erytomatosis, Sjoegren's syndrome, psoriasis, inflammatory bowel disease, including Crohn's disease, colitis, e.g. ulcerative colitis; sepsis, septic shock, autoimmune hemolytic anemia (AHA), autoantibody triggered urticaria, pemphigus, nephritis, glomerulonephritis, Goodpastur syndrom, ankylosing spondylitis, Reiter's syndrome, polymyositis, dermatomyositis, cytokine-mediated toxicity, interleukin-2 toxicity, alopecia areata, uveitis, lichen planus, bullous pemphigoid, myasthenia gravis, type I diabetes mellitus, immune-mediated infertility such as premature ovarian failure, polyglandular failure, hypothyroidism, pemphigus vulgaris, pemphigus I-oliaceus, paraneoplastic pemphigus, autoimnune hepatitis including that associated with hepatitis B virus (HBV) and hepatitis C virus (HCV), Addison's disease, autoimmune skin diseases, such as psoriasis, dermatitis herpetiformis, epidermolysis bullosa, linear IgA bullous dermatosis, epidermolysis bullosa acquisita, chronic bullous disease of childhood, pernicious anemia, hemolytic anemia, vitiligo, type I, type II and type III autoimmune polyglandular syndromes, Autoimmune Hypoparathyroidism, Autoimmune Hypophysitis, Autoimmune Oophoritis, Autoimmune Orchitis, pemphigoid gestationis, cicatricial pemphigoid, mixed essential cryoglobulinemia, immune thrombocytopenic purpura, Goodpasture's syndrome, autoimmune neutropenia, Eaton-Lambert myasthenic syndrome, stiff-man syndrome, encephalomyelitis, acute disseminated encephalomyelitis, Guillain-Barre syndrome, cerebellar degeneration, retinopathy, primary biliary sclerosis, sclerosing cholangitis autoimmune hepatitis, gluten-sensitive enteropathy, reactive arthritides, polymyositis/dermatomyositis, mixed connective tissue disease, Bechet's syndrome, polyarteritis nodosa allergic anguitis and granulomatosis (Churg-Strauss disease), polyangiitis overlap syndrome (hypersensitivity) vasculitis, Wegener's granulomatosis, temporal arteritis Kawasaki's disease, sarcoidosis, cryopathies, Celiac disease, disorders associated with inflammation e.g. including (chronic) inflammatory disorders, disorders related with the inflammation of the bronchi, e.g. including bronchitis, cervix, e.g. including cervicitis, conjunctiva, e.g. conjunctivitis, esophagus, e.g. esophagitis, heart muscle, e.g. myocarditis, rectum, e.g. proctitis, sclera, e.g. scleritis, gums, involving bone, pulmonary inflammation (alveolitis), airways, e.g. asthma, such as bronchial asthma, acute respiratory distress syndrome (ARDS), inflammatory skin disorders such as contact hypersensitivity, atopic dermatitis; fibrotic disease (e.g., pulmonary fibrosis), encephilitis, inflammatory osteolysis, disorders associated with the brain and the nerves, neurodegenerative disorders, e.g. including disorders of the central nervous system as well as disorders of the peripheral nervous system, e.g. CNS disorders including central nervous system infections, brain injuries, cerebrovascular disorders and their consequences, Parkinson's disease, corticobasal degeneration, motor neuron disease, dementia including ALS, multiple sclerosis, traumatic disorders, including trauma and inflammatory consequences of trauma, traumatic brain injury, stroke, post-stroke, post-traumatic brain injury, small-vessel cerebrovascular disease, eating disorders; further dementias, e.g. including Alzheimer's disease, vascular dementia, dementia with Lewy-bodies, frontotemporal dementia and Parkinsonism linked to chromosome 17, frontotemporal dementias, including Pick's disease, progressive nuclear palsy, corticobasal degeneration, Huntington's disease, thalamic degeneration, Creutzfeld Jakob dementia, HIV dementia, schizophrenia with dementia, Korsakoffs psychosis, cognitive-related disorders, such as mild cognitive impairment, age-associated memory impairment, age-related cognitive decline, vascular cognitive impairment, attention deficit disorders, attention deficit hyperactivity disorders, and memory disturbances in children with learning disabilities; conditions associated with the hypothalamic-pituitary-adrenal axis, neuronal disorders, e.g. including neuronal migration disorders, hypotonia (reduced muscle tone), muscle weakness, seizures, developmental delay (physical or mental development difficulty), mental retardation, growth failure, feeding difficulties, lymphedema, microcephaly, symptoms affecting the head and the brain, motor dysfunction;

disorders associated with the respiratory tract and lung e.g. including pulmonary disorders, chronic pulmonary disease, fibrosing aveolitis, lung fibrosis, disorders associated with cancer and cell overproliferation, e.g. including premalignant conditions, hyperproliferative disorders, cancers whether primary or metastatic, cervical and metastatic cancer, cancer originating from uncontrolled cellular proliferation, solid tumors, such as such as described in WO02066019, including nonsmall cell lung cancer, cervical cancer; tumor growth, lymphoma, B-cell or T-cell lymphoma, benign tumors, benign dysproliferative disorders, renal carcinoma, esophageal cancer, stomach cancer, renal carcinoma, bladder cancer, breast cancer, colon cancer, lung cancer, melanoma, nasopharyngeal cancer, osteocarcinoma, ovarian cancer, uterine cancer; prostate cancer, skin cancer, leukemia, tumor neovascularization, angiomas, myelodysplastic disorders, unresponsiveness to normal death-inducing signals (immortalization), increased cellular motility and invasiveness, genetic instability, dysregulated gene expression, (neuro)endocrine cancer (carcinoids), blood cancer, lymphocytic leukemias, neuroblastoma; soft tissue cancer, prevention of metastasis, disorders associated with angiogenesis, e.g. including insufficient ability to recruit blood supply, disorders characterized by odified angiogenesis, tumor associated angiogenesis, disorders associated with infectious disorders, e.g. including bacterial disorders, otitis media, Lyme disease, thryoditis, viral disorders, parasitic disorders, fungal disorders, malaria, e.g. malaria anemia, sepsis, severe sepsis, septic shock, e.g. endotoxin-induced septic shock, exotoxin-induced toxic shock, infective (true septic) shock, septic shock caused by Gram-negative bacteria, pelvic inflammatory disease, AIDS, enteritis, pneumonia; meningitis, encephalitis, disorders associated with rheumatic disorders, e.g. including arthritis, rheumatoid arthritis, osteoarthritis, psoriatic arthritis, crystal arthropathies, gout, pseudogout, calcium pyrophosphate deposition disease, lupus syndromes, systemic lupus erythematosus, sclerosis, sclerodema, multiple sclerosis, artheroscierosis, arteriosclerosis, spondyloarthropathies, systemic sclerosis, reactive arthritis, Reiter's syndrome, ankylosing spondylitis, polymyositis, disorders associated with transplantation, e.g. including transplant rejection crisis and other disorders following transplantation, such as organ or tissue (xeno) transplant rejection, e.g. for the treatment of recipients of e.g. heart, lung, combined heart-lung, liver, kidney, pancreatic, skin, corneal transplants, graft versus host disease, such as following bone marrow transplantation, ischemic reperfusion injury.

In another aspect the present invention provides a compound of the present invention for use as a pharmaceutical, the use of a compound of the present invention as a pharmaceutical e.g. for the treatment of disorders mediated by sphingomyelinase (aSMase) activity.

For pharmaceutical use one or more compounds of the present invention may be used, e.g. one, or a combination of two or more compounds of the present invention, preferably one compound of the present invention is used.

A compound of the present invention may be used as a pharmaceutical in the form of a pharmaceutical composition.

In another aspect the present invention provides a pharmaceutical composition comprising a compound of the present invention in association with at least one pharmaceutically acceptable excipient, e.g. appropriate carrier and/or diluent, e.g. including fillers, binders, disintegrants, flow conditioners, lubricants, sugars or sweeteners, fragrances, preservatives, stabilizers, wetting agents and/or emulsifiers, solubilizers, salts for regulating osmotic pressure and/or buffers.

In another aspect the present invention provides
- a pharmaceutical composition of the present invention for use of treating disorders which are mediated by sphingomyelinase (aSMase) activity.
- the use of a pharmaceutical composition of the present invention for treating disorders which are mediated by sphingomyelinase (aSMase) activity.

In a further aspect the present invention provides a method of treating disorders which are mediated by sphingomyelinase (aSMase) activity, e.g. including disorders as specified above, which treatment comprises administering to a subject in need of such treatment an effective amount of a compound of the present invention; e.g. in the form of a pharmaceutical composition.

In another aspect the present invention provides
- a compound of the present invention for the manufacture of a medicament,
- the use of a compound of the present invention for the manufacture of a medicament, e.g. a pharmaceutical composition, for the treatment of disorders, which are mediated by sphingomyelinase (aSMase) activity.

Treatment includes treatment and prophylaxis (prevention).

For such treatment, the appropriate dosage will, of course, vary depending upon, for example, the chemical nature and the pharmakokinetic data of a compound of the present invention used, the individual host, the mode of administration and the nature and severity of the conditions being treated. However, in general, for satisfactory results in larger mammals, for example humans, an indicated daily dosage includes a range
- from about 0.0001 g to about 1.5 g, such as 0.001 g to 1.5 g;
- from about 0.001 mg/kg body weight to about 20 mg/kg body weight, such as 0.01 mg/kg body weight to 20 mg/kg body weight, for example administered in divided doses up to four times a day.

A compound of the present invention may be administered to larger mammals, for example humans, by similar modes of administration than conventionally used with other mediators, e.g. low molecular weight inhibitors, of sphingomyelinase (aSMase) activity.

A compound of the present invention may be administered by any conventional route, for example enterally, e.g. including nasal, buccal, rectal, oral, administration; parenterally, e.g. including intravenous, intraarterial, intramuscular, intracardiac, subcutanous, intraosseous infusion, transdermal (diffusion through the intact skin), transmucosal (diffusion through a mucous membrane), inhalational administration; topically; e.g. including epicutaneous, intranasal, intratracheal administration; intraperitoneal (infusion or injection into the peritoneal cavity); epidural (peridural) (injection or infusion into the epidural space); intrathecal (injection or infusion into the cerebrospinal fluid); intravitreal (administration via the eye); or via medical devices, e.g. for local delivery, e.g. stents, e.g. in form of coated or uncoated tablets, capsules, (injectable) solutions, infusion solutions, solid solutions, suspensions, dispersions, solid dispersions; e.g. in the form of ampoules, vials, in the form of creams, gels, pastes, inhaler powder, foams, tinctures, lip sticks, drops, sprays, or in the form of suppositories.

For topical use, e.g. including administration to the eye, satisfactory results may be obtained with local administration of a 0.5-10%, such as 1-3% concentration of active substance several times daily, e.g. 2 to 5 times daily.

The compounds of the present invention may be administered in the form of a pharmaceutically acceptable salt, or in free form; optionally in the form of a solvate. A compound of the present invention in the form of a salt and/or in the form of a solvate exhibits the same order of activity as a compound of the present invention in free form.

A compound of the present invention may be used for any method or use as described herein alone or in combination with one or more, at least one, other, second drug substance.

In another aspect the present invention provides
- A combination of a compound of the present invention with at least one second drug substance;
- A pharmaceutical combination comprising a compound of the present invention in combination with at least one second drug substance;
- A pharmaceutical composition comprising a compound of the present invention in combination with at least one second drug substance and one or more pharmaceutically acceptable excipient(s);
- A compound of the present invention in combination with at least one second drug substance, e.g. in the form of a pharmaceutical combination or composition, for use in any method as defined herein, e.g.
- A combination, a pharmaceutical combination or a pharmaceutical composition, comprising a compound of the present invention and at least one second drug substance for use as a pharmaceutical;
- The use as a pharmaceutical of a compound of the present invention in combination with at least one second drug substance, e.g. in the form of a pharmaceutical combination or composition;
- A method for treating disordes mediated by sphingomyelinase (aSMase) activity in a subject in need thereof, comprising co-administering, concomitantly or in sequence, a therapeutically effective amount of a compound of the present invention and at least one second drug substance, e.g. in the form of a pharmaceutical combination or composition;
- A compound of the present invention in combination with at least one second drug substance, e.g. in the form of a pharmaceutical combination or composition, for use in the preparation of a medicament for use in disorders mediated by sphingomyelinase (aSMase) activity.

Combinations include fixed combinations, in which a compound of the present invention and at least one second drug substance are in the same formulation; kits, in which a compound of the present invention and at least one second drug substance in separate formulations are provided in the same package, e.g. with instruction for co-administration; and free combinations in which a compound of the present invention and at least one second drug substance are packaged separately, but instruction for concomitant or sequential administration are given.

In another aspect the present invention provides

A pharmaceutical package comprising a first drug substance which is a compound of the present invention and at least one second drug substance, beside instructions for combined administration;

A pharmaceutical package comprising a compound of the present invention beside instructions for combined administration with at least one second drug substance;

A pharmaceutical package comprising at least one second drug substance beside instructions for combined administration with a compound of the present invention.

Treatment with combinations according to the present invention may provide improvements compared with single treatment.

In another aspect the present invention provides

A pharmaceutical combination comprising an amount of a compound of the present invention and an amount of a second drug substance, wherein the amounts are appropriate to produce a synergistic therapeutic effect;

A method for improving the therapeutic utility of a compound of the present invention comprising co-administering, e.g. concomitantly or in sequence, of a therapeutically effective amount of a compound of the present invention and a second drug substance.

A method for improving the therapeutic utility of a second drug substance comprising co-administering, e.g. concomitantly or in sequence, of a therapeutically effective amount of a compound of the present invention and a second drug substance.

A combination of the present invention and a second drug substance as a combination partner may be administered by any conventional route, for example as set out above for a compound of the present invention. A second drug may be administered in dosages as appropriate, e.g. in dosage ranges which are similar to those used for single treatment, or, e.g. in case of synergy, even below conventional dosage ranges.

Pharmaceutical compositions according to the present invention may be manufactured according, e.g. analogously, to a method as conventional, e.g. by mixing, granulating, coating, dissolving or lyophilizing processes. Unit dosage forms may contain, for example, from about 0.1 mg to about 1500 mg, such as 0.1 mg to about 1000 mg. Pharmaceutical compositions comprising a combination of the present invention and pharmaceutical compositions comprising a second drug as described herein, may be provided as appropriate, e.g. according, e.g. analogously, to a method as conventional, or as described herein for a pharmaceutical composition of the present invention.

By the term "second drug substance" is meant a chemotherapeutic drug, especially any chemotherapeutic agent other than a compound of the present invention, such as a compound of formula I.

For example, a second drug substance as used herein includes immunomodulatory drugs, anticancer drugs other inhibitors of sphingomyelinase (aSMase) activity, than compounds of the present inventions, e.g. including antibodies and low molecular weight compounds.

Anti-inflammatory and/or immunomodulatory drugs which are prone to be useful in combination with a compound of the present invention include e.g.

mediators, e.g. inhibitors, of mTOR activity, including rapamycin of formula

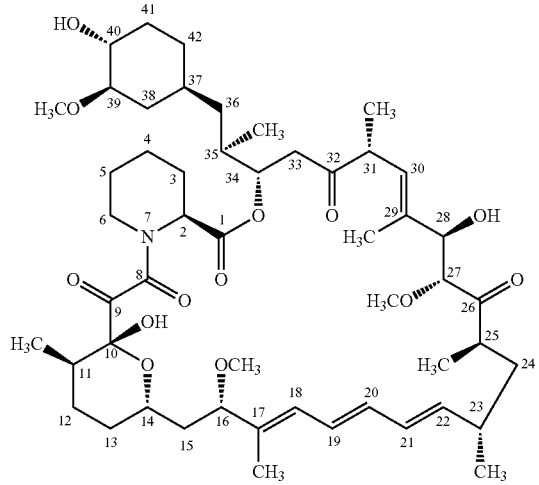

and rapamycin derivatives, e.g. including

40-O-alkyl-rapamycin derivatives, such as 40-O-hydroxyalkyl-rapamycin derivatives, e.g. 40-O-(2-hydroxy)-ethyl-rapamycin (everolimus), 40-O-alkoxyalkyl-rapamycin derivatives, e.g. 40-O-ethoxyethyl-rapamycin (Biolomus A9), 32-deoxo-rapamycin derivatives and 32-hydroxy-rapamycin derivatives, such as 32-deoxorapamycin, 16-O-substituted rapamycin derivatives such as 16-pent-2-ynyloxy-32-deoxorapamycin, 16-pent-2-ynyloxy-32 (S or R)-dihydro-rapamycin, 16-pent-2-ynyloxy-32 (S or R)-dihydro-40-O-(2-hydroxyethyl)-rapamycin, rapamycin derivatives which are acylated at the oxygen group in position 40, e.g. 40-[3-hydroxy-2-(hydroxy-methyl)-2-methylpropanoate]-rapamycin (also known as CCI779), rapamycin derivatives which are substituted in 40 position by heterocyclyl, e.g. 40-epi-(tetrazolyl)-rapamycin (also known as ABT578), the so-called rapalogs, e.g. as disclosed in WO9802441, WO0114387 and WO0364383, such as AP23573, and compounds disclosed under the name TAFA-93, AP23464, AP23675 and AP23841;

mediators, e.g. inhibitors, of calcineurin, e.g. cyclosporin A, FK506 (tacrolimus, Prograf®, Advagraf®), ISA-247 (voclosporin);

ascomycins having immuno-suppressive properties, e.g. ABT-281, ASM981;

corticosteroids; e.g. including prasterone (dehydroepiandrosterone), cyclophosphamide;

cyclophosphamid IV (Revimmune®), azathioprene; leflunomide; FK778, mizoribine;

mycophenolic acid or salt; e.g. sodium, mycophenolate mofetil (CellCept®);

15-deoxyspergualine or an immunosuppressive homologue, analogue or derivative thereof;

mediators, e.g. inhibitors, of bcr-abl tyrosine kinase activity;

mediators, e.g. inhibitors, of c-kit receptor tyrosine kinase activity;

mediators, e.g. inhibitors, of PDGF receptor tyrosine kinase activity, e.g. Gleevec (imatinib);

mediators, e.g. inhibitors, of p38 MAP kinase activity, mediators, e.g. inhibitors, of VEGF receptor tyrosine kinase activity, mediators, e.g. inhibitors, of PKC activity, e.g. as disclosed in WO0238561 or WO0382859, e.g. the compound of Example 56 or 70;

mediators, e.g. inhibitors, of JAK3 kinase activity, e.g. N-benzyl-3,4-dihydroxy-benzylidene-cyanoacetamide α-cyano-(3,4-dihydroxy)-]N-benzylcinnamamide (Tyrphostin AG 490), prodigiosin 25-C (PNU156804), [4-(4'-hydroxyphenyl)-amino-6,7-dimethoxyquinazoline] (WHI-P131), [4-(3'-bromo-4'-hydroxylphenyl)-amino-6,7-dimethoxyquinazoline] (WHI-P154), [4-(3',5'-dibromo-4'-hydroxylphenyl)-amino-6,7-dimethoxyquinazoline] WHI-P97, KRX-211, 3-{(3R,4R)-4-methyl-3-[methyl-(7H-pyrrolo[2,3-d]pyrimidin-4-yl)-amino]-piperidin-1-yl}-3-oxo-propionitrile, in free form or in a pharmaceutically acceptable salt form, e.g. mono-citrate (also called CP-690,550), or a compound as disclosed in WO2004052359 or WO2005066156;

mediators, e.g. agonists or modulators of S1P receptor activity, e.g. FTY720 optionally phosphorylated or an analog thereof, e.g. 2-amino-2-[4-(3-benzyloxyphenylthio)2-chlorophenyl]ethyl-1,3-propanediol optionally phosphorylated or 1-{4-[1-(4-cyclohexyl-3-trifluoromethyl-benzyloxyimino)ethyl]-2-ethyl-benzyl}-azetidine-3-carboxylic acid or its pharmaceutically acceptable salts;

immunosuppressive monoclonal antibodies, e.g., monoclonal antibodies to leukocyte receptors, e.g. Blys receptor, such as belimumab, lymphostat B, BAFF receptor, MHC, CD2, CD3, e.g. visilizumab, CD4, e.g. zanolimumab, CD7, CD8, CD11a, e.g. efalizumab (Raptiva®), CD20, e.g. rituximab (Rituxan®, Mabthera), ibritumomab tiuxetan conjugated to $^{111}$In or $^{90}$Y (Zevalin®), $^{131}$I tositumumab (Bexxar®), C025, CD28, CD33, e.g. gemtuzumab (Mylotarg®, CD40, e.g. ant-CD40L or anti CD154, such as IDEC-131, CD45, CD52, CD54, e.g. Alemtuzumab (Campath-I®), CD58, CD80, CD86, IL-2 receptor, e.g. daclizumab (Zenapax®), IL6 receptor (e.g. tocilizumab, Actemra®), IL-12 receptor, IL-17 receptor, IL-23 receptor or their ligands; e.g. antibodies to IL-12, IL-23, such as ABT-874, CNTO 1275 (IL-12/IL23 mAb), IL-10, such as B-N10, e.g. antibodies to double-stranded DNA (dsDNA), such as abetimus sodium (Riquent®)), other compounds affecting the immune system, such as a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; or an anti-CTLA4 agent, such as ipilimumab, ticilimumab, glatirameracetat (copolymer-1, Copaxone®), MBP8298 (a synthetic peptide), laquinimod (ABR-215062), vaccines having immunomodulatory activity, e.g. Tovaxin®, NeuroVax®, pirfenidone, BG-12 (an oral fumarate), mediators, e.g. inhibitors of adhesion molecule activities, e.g. LFA-1 antagonists, ICAM-1 or -3 antagonists, VCAM-4 antagonists or VLA-4 antagonists, mediators, e.g. antagonists of CCR9 acitiviy, mediators, e.g. inhibitors, of MIF activity, 5-aminosalicylate (5-ASA) agents, such as sulfasalazine, Azulfidine®, Asacol®, Dipentum®, Pentasa®, Rowasa®, Canasa®, Colazal®, e.g. drugs containing mesalamine; e.g. mesalazine in combination with heparin;

mediators, e.g. inhibitors, of TNF-alpha activity, such as RPL228 (Rosanto, York Pharma), e.g. including antibodies which bind to TNF-alpha, e.g. infliximab (Remicade®), thalidomide, lenalidomide, golimumab, adalimumab (Humira®), fully human immunoglobulin G (IgG1) monoclonal antibody that is specific for human TNF alpha), etanercept (Enbrel®), alefacept (Amevive®), certolizumab pegol (Cimzia®, CDP 870), afelimomab, AME527 (Lilly), anti-TNF domain antibody PN0621, nitric oxide releasing non-steriodal anti-inflammatory drugs (NSAIDs), e.g. including COX-inhibiting NO-donating drugs (CINOD);

phospordiesterase, e.g. mediators, such as inhibitors of PDE4B activity, mediators, e.g. inhibitors, of caspase activity, mediators, e.g. agonists, of the G protein coupled receptor GPBAR1, mediators, e.g. inhibitors, of ceramide kinase activity, 'multi-functional anti-inflammatory' drugs (MFAIDs), e.g. cytosolic phospholipase A2 (cPLA2) inhibitors, such as membrane-anchored phospholipase A2 inhibitors linked to glycosaminoglycans;

antibiotics and antifungals, such as penicillins, cephalosporins, erythromycins, tetracyclines, sulfonamides, such as sulfadiazine, sulfisoxazole; sulfones, such as dapsone; pleuromutilins, fluoroquinolones, e.g. metronidazole, quinolones such as ciprofloxacin; levofloxacin; probiotics, commensal bacteria e.g. *Lactobacillus, Lactobacillus reuteri*; micafungin, antiviral drugs, such as ribivirin, vidarabine, acyclovir, ganciclovir, zanamivir, oseltamivir phosphate, famciclovir, atazanavir, amantadine, didanosine, efavirenz, foscamet, indinavir, lamivudine, nelfinavir, ritonavir, saquinavir, stavudine, valacyclovir, valganciclovir, civacir, zidovudine, antibodies against RSV protein, e.g. RSV F protein, such as palivizumab (Synagis®), motavizumab, mediators, e.g. inhibitors of the blood protein "complement 5(a)", such as eculizumab, pexelizumab, serum phosphorus controlling agents, e.g. sevelamer carbonate (Renagel®); phosphate binders that reduces high serum phosphate levels in renal disease patients, such as lanthanum carbonate (Fosrenol®).

mediators, e.g. agonists, of GPBAR1 mediator activity, e.g. including antibodies and low molecular weight compounds;

mediators, e.g. inhibitors of ceramide kinase activity, e.g. including antibodies and low molecular weight compounds, alpha-4-integrin antibodies, e.g. natalizumab (Tysabri®.

an erythropoiesis stimulating protein, such as epoietin (Procrit®), EPOETIN ALFA, (Epogen®), darbepoetin alfa (Aranesp®), T-cell co-stimulation modulators, such as abatacept (Orencia®), modulators, e.g. inhibitors, of acid sphingomyelinase (aS-Mase), which are different from the compounds of the present invention, Anti-inflammatory drugs which are prone to be useful in combination with a compound of the present invention include e.g. non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); cyclooxygenase-2 (COX-2) inhibitors such as celecoxib; inhibitors of phosphodiesterase type IV (PDE-IV); e.g. MN-166, antagonists of the chemokine receptors, especially CCR1, e.g. ZK811752 (BX-471), CCR2, and CCR3; cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrate, fenofibrate and benzafibrate), and probucol; anticholinergic agents such as muscarinic antagonists (ipratropium bromide); other compounds such as theophylline, sulfasalazine and aminosalicylates, e.g. 5-aminosalicylic acid and prodrugs thereof, antirheumatics, IgE antibodies, e.g. omalizumab (Xolair®).

Anticancer drugs which are prone to be useful as a combination partner with a compound of the present invention, e.g. prone to be useful according to the present invention, e.g. include i. a steroid; e.g. prednisone.

ii. an adenosine-kinase-inhibitor; which targets, decreases or inhibits nucleobase, nucleoside, nucleotide and nucleic acid metabolisms, such as 5-Iodotubercidin, which is also known as 7H-pyrrolo[2,3-d]pyrimidin-4-amine, 5-iodo-7-β-D-ribofuranosyl.

iii. an adjuvant; which enhances the 5-FU-TS bond as well as a compound which targets, decreases or inhibits, alkaline phosphatase, such as leucovorin, levamisole; and other adjuvants used in cancer chemotherapy adjuvants, such as mesna (Uromitexan®, Mesnex®).

iv. an adrenal cortex antagonist; which targets, decreases or inhibits the activity of the adrenal cortex and changes the peripheral metabolism of corticosteroids, resulting in a decrease in 17-hydroxycorticosteroids, such as mitotane.

v. an AKT pathway inhibitor; such as a compound which targets, decreases or inhibits Akt, also known as protein kinase B (PKB), such as deguelin, which is also known as 3H-bis[1]benzopyrano[3,4-b:6',5'-e]pyran-7(7aH)-one, 13,13a-dihydro-9,10-dimethoxy-3,3-dimethyl-, (7aS, 13aS); and triciribine, which is also known as 1,4,5,6,8-pentaazaacenaphthylen-3-amine, 1,5-dihydro-5-methyl-1-β-D-ribofuranosyl; KP372-1 (QLT394).

vi. an alkylating agent; which causes alkylation of DNA and results in breaks in the DNA molecules as well as cross-linking of the twin strands, thus interfering with DNA replication and transcription of RNA, such as chlorambucil, chlormethine, cyclophosphamide, ifosfamide, melphalan, estramustine; nitrosueras, such as carmustine, fotemustine, lomustine, streptozocin (streptozotocin, STZ), BCNU; Gliadel; dacarbazine, mechlorethamine, e.g. in the form of a hydrochloride, procarbazine, e.g. in the form of a hydrochloride, thiotepa, temozolomide, nitrogen mustard, mitomycin, altretamine, busulfan, estramustine, uramustine. Cyclophosphamide can be administered, e.g., in the form as it is marketed, e.g., under the trademark CYCLOSTIN®; ifosfamide as HOLOXAN®, temozolomide as TEMODAR®, nitrogen mustard as MUSTARGEN®, estramustine as EMYCT®, streptozocin as ZANOSAR®D.

vii. an angiogenesis inhibitor; which targets, decreases or inhibits the production of new blood vessels, e.g. which targets methionine aminopeptidase-2 (MetAP-2), macrophage inflammatory protein-1 (MIP-1alpha), CCL5, TGF-beta, lipoxygenase, cyclooxygenase, and topoisomerase, or which indirectly targets p21, p53, CDK2 and collagen synthesis, e.g. including fumagillin, which is known as 2,4,6,8-decatetraenedioic acid, mono[(3R,4S,5S,6R)-5-methoxy-4-[(2R,3R)-2-methyl-3-(3-methyl-2-butenyl)oxiranyl]-1-oxaspiro[2.5]oct-6-yl]ester, (2E,4E,6E,8E)-(9Cl); shikonin, which is also known as 1,4-naphthalenedione, 5,8-dihydroxy-2-[(1R)-1-hydroxy-4-methyl-3-pentenyl]-(9Cl); tranilast, which is also known as benzoic acid, 2-[[3-(3,4-dimethoxyphenyl)-1-oxo-2-propenyl]amino]; ursolic acid; suramin; bengamide or a derivative thereof, thalidomide, TNP-470.

viii. an anti-androgen; which blocks the action of androgens of adrenal and testicular origin which stimulate the growth of normal and malignant prostatic tissue, such as nilutamide; bicalutamide (CASODEX®), which can be formulated, e.g., as disclosed in U.S. Pat. No. 4,636,505.

ix. an anti-estrogen; which antagonizes the effect of estrogens at the estrogen receptor level, e.g. including an aromatase inhibitor, which inhibits the estrogen production, i.e. the conversion of the substrates androstenedione and testosterone to estrone and estradiol, respectively, e.g. including atamestane, exemestane, formestane, aminoglutethimide, roglethimide, pyridoglutethimide, trilostane, testolactone, ketoconazole, vorozole, fadrozole, anastrozole, letrozole, toremifene; bicalutamide; flutamide; tamoxifen, tamoxifen citrate; tamoxifen; fulvestrant; raloxifene, raloxifene hydrochloride. Tamoxifen may be e.g. administered in the form as it is marketed, e.g., NOLVADEX®; and raloxifene hydrochloride is marketed as EVISTA®. Fulvestrant may be formulated as disclosed in U.S. Pat. No. 4,659,516 and is marketed as FASLODEX®.

x. an anti-hypercalcemia agent; which is used to treat hypercalcemia, such as gallium (III) nitrate hydrate; and pamidronate disodium.

xi. an antimetabolite; which inhibits or disrupts the synthesis of DNA resulting in cell death. Examples of an antimetabolite include, but are not limited to, DNA de-methylating agents and folic acid antagonists, e.g. methotrexate, pemetrexed, (permetrexed, Alimta®), raltitrexed; purins, e.g. 6-mercaptopurine, cladribine, clofarabine; fludarabine, thioguanine (tioguanine), 6-thioguanine, nelarabine (compound 506), tiazofurin (inhibits inosine monophosphate dehydrogenase and guanosine triphosphate pools), pentostatin (deoxycoformycin); cytarabine; flexuridine; fluorouracil; 5-fluorouracil (5-FU), floxuridine (5-FUdR), capecitabine; gemcitabine; gemcitabine hydrochloride; hydroxyurea (e.g. Hydrea®); DNA de-methylating agents, such as 5-azacytidine (Vidaza®) and decitabine; fluoromethylene deoxycitidine (FmdC), 5-aza-2'-deoxycytidine, troxacitabine (L-isomer cytosine analogue), edatrexate; Capecitabine and gemcitabine can be administered e.g. in the marketed form, such as XELODA® and GEMZAR®.

xii. an apoptosis inducer; which induces the normal series of events in a cell that leads to its death, e.g. selectively inducing the X-linked mammalian inhibitor of apoptosis protein XIAP, or e.g. downregulating BCL-xL; such as ethanol, 2-[[3-(2,3-dichlorophenoxy)propyl]amino];

gambogic acid; embelin, which is also known as 2,5-cyclohexadiene-1,4-dione, 2,5-dihydroxy-3-undecyl; arsenic trioxide arsenic trioxide (TRISENOX®).

xiii. an aurora kinase inhibitor; which targets, decreases or inhibits later stages of the cell cycle from the G2/M check point all the way through to the mitotic checkpoint and late mitosis; such as binucleine 2, which is also known as methanimidamide, N'-[1-(3-chloro-4-fluorophenyl)-4-cyano-1H-pyrazol-5-yl]-N,N-dimethyl.

xiv. a Bruton's Tyrosine Kinase (BTK) inhibitor; which targets, decreases or inhibits human and murine B cell development; such as terreic acid.

xv. a calcineurin inhibitor; which targets, decreases or inhibits the T cell activation pathway, such as cypermethrin, which is also known as cyclopropanecarboxylic acid, 3-(2,2-dichloroethenyl)-2,2-dimethyl-, cyano(3-phenoxyphenyl)methyl ester; deltamethrin, which is also known as cyclopropanecarboxylic aci, 3-(2,2-dibromoethenyl)-2,2-dimethyl-(S)-cyano(3-phenoxyphenyl)methyl ester, (1R,3R); fenvalerate, which is also known as benzeneacetic acid, 4-chloro-α-1-methylethyl)-cyano(3-phenoxyphenyl)methyl ester; and Tyrphostin 8; but excluding cyclosporin or FK506.

xvi. a CaM kinase II inhibitor; which targets, decreases or inhibits CaM kinases; constituting a family of structurally related enzymes that include phosphorylase kinase, myosin light chain kinase, and CaM kinases I-IV; such as 5-isoquinolinesulfonic acid, 4-[(2S)-2-[(5-isoquinolinylsulfonyl)methylamino]-3-oxo-3-(4-phenyl-1-piperazinyl)propyl]phenyl ester (9Cl); benzenesulfonamide, N-[2-[[[3-(4-chlorophenyl)-2-propenyl]methyl]amino]methyl]phenyl]-N-(2-hydroxyethyl)-4-methoxy.

xvii. a CD45 tyrosine phosphatase inhibitor; which targets, decreases or inhibits dephosphorylating regulatory pTyr residues on Src-family protein-tyrosine kinases, which aids in the treatment of a variety of inflammatory and immune disorders; such as phosphonic acid, [[2-(4-bromophenoxy)-5-nitrophenyl]hydroxymethyl].

xviii. a CDC25 phosphatase inhibitor; which targets, decreases or inhibits overexpressed dephosphorylate cyclin-dependent kinases in tumors; such as 1,4-naphthalenedione, 2,3-bis[(2-hydroyethyl)thio].

xix. a CHK kinase inhibitor; which targets, decreases or inhibits overexpression of the antiapoptotic protein Bcl-2; such as debromohymenialdisine. Targets of a CHK kinase inhibitor are CHK1 and/or CHK2. An example of a CHK kinase inhibitor includes, but is not limited to, debromohymenialdisine.

xx. a controlling agent for regulating genistein, olomucine and/or tyrphostins; such as daidzein, which is also known as 4H-1-benzopyran-4-one, 7-hydroxy-3-(4-hydroxyphenyl); Iso-Olomoucine, and Tyrphostin 1.

xxi. a cyclooxygenase inhibitor; e.g. including Cox-2 inhibitors; which targets, decreases or inhibits the enzyme Cox-2 (cyclooxygenase-2); such as 1H-indole-3-acetamide, 1-(4-chlorobenzoyl)-5-methoxy-2-methyl-N-(2-phenylethyl); 5-alkyl substituted 2-arylaminophenylacetic acid and derivatives, e.g. celecoxib (CELEBREX®), rofecoxib (VIOXX®), etoricoxib, valdecoxib; or a 5-alkyl-2-arylaminophenylacetic acid, e.g., 5-methyl-2-(2'-chloro-6'-fluoroanilino)phenyl acetic acid, lumiracoxib; and celecoxib.

xxii. a cRAF kinase inhibitor; which targets, decreases or inhibits the up-regulation of E-selectin and vascular adhesion molecule-1 induced by TNF; such as 3-(3,5-dibromo-4-hydroxybenzylidene)-5-iodo-1,3-dihydroindol-2-one; and benzamide, 3-(dimethylamino)-N-[3-[(4-hydroxybenzoyl)amino]-4-methylphenyl]. Raf kinases play an important role as extracellular signal-regulating kinases in cell differentiation, proliferation, and apoptosis. A target of a cRAF kinase inhibitor includes, but is not limited, to RAF1. RAF kinase inhibitors e.g. include compounds as described in WO2005028444 or WO0009495.

xxiii. a cyclin dependent kinase inhibitor; which targets, decreases or inhibits cyclin dependent kinase playing a role in the regulation of the mammalian cell cycle; such as N9-isopropyl-olomoucine; olomoucine; purvalanol B, which is also known as Benzoic acid, 2-chloro-4-[[2-[[(1R)-1-(hydroxymethyl)-2-methylpropyl]amino]-9-(1-methylethyl)-9H-purin-6-yl]amino]-(9Cl); roascovitine; indirubin, which is also known as 2H-indol-2-one, 3-(1,3-dihydro-3-oxo-2H-indol-2-ylidene)-1,3-dihydro-; kenpaullone, which is also known as indolo[3,2-d][1]benzazepin-6(5H)-one, 9-bromo-7,12-dihydro-; purvalanol A, which is also known as 1-Butanol, 2-[[6-[(3-chlorophenyl)amino]-9-(1-methylethyl)-9H-purin-2-yl]amino]-3-methyl-, (2R)-; indirubin-3'-monooxime. Cell cycle progression is regulated by a series of sequential events that include the activation and subsequent inactivation of cyclin dependent kinases (Cdks) and cyclins. Cdks are a group of serine/threonine kinases that form active heterodimeric complexes by binding to their regulatory subunits, cyclins. Examples of targets of a cyclin dependent kinase inhibitor include, but are not limited to, CDK, AHR, CDK1, CDK2, CDK5, CDK4/6, GSK3beta, and ERK.

xxiv. a cysteine protease inhibitor; which targets, decreases or inhibits cystein protease which plays a vital role in mammalian cellular turnover and apoptosis; such as 4-morpholinecarboxamide, N-[(1S)-3-fluoro-2-oxo-1-(2-phenylethyl)propyl]amino]-2-oxo-1-(phenylmethyl)ethyl].

xxv. a DNA intercalator; which binds to DNA and inhibits DNA, RNA, and protein synthesis; such as plicamycin, dactinomycin.

xxvi. a DNA strand breaker; which causes DNA strand scission and results in inhibition of DNA synthesis, ininhibition of RNA and protein synthesis; such as bleomycin.

xxvii. an E3 Ligase inhibitor; which targets, decreases or inhibits the E3 ligase which inhibits the transfer of ubiquitin chains to proteins, marking them for degradation in the proteasome; such as N-((3,3,3-trifluoro-2-trifluoromethyl)propionyl)sulfanilamide.

xxviii. an endocrine hormone; which by acting mainly on the pituitary gland causes the suppression of hormones in males, the net effect being a reduction of testosterone to castration levels; in females, both ovarian estrogen and androgen synthesis being inhibited; such as leuprolide; megestrol, megestrol acetate.

xxix. compounds targeting, decreasing or inhibiting the activity of the epidermal growth factor family of receptor tyrosine kinases (EGFR, ErbB2, (HER-2), ErbB3, ErbB4 as homo- or heterodimers), such as compounds, proteins or antibodies which inhibit members of the EGF receptor tyrosine kinase family, e.g. EGF receptor, ErbB1, ErbB2, ErbB3 and ErbB4 or bind to EGF or EGF-related ligands, and are in particular those compounds, proteins or monoclonal antibodies generically and specifically disclosed in WO9702266, e.g. the compound of ex. 39, EP0564409, WO9903854, EP0520722, EP0566226, EP0787722, EP0837063, U.S. Pat. No.

5,747,498, WO9810767, WO9730034, WO9749688, WO9738983 and, especially, WO9630347, e.g. a compound known as CP 358774, WO9633980, e.g. a compound known as ZD 1839; and WO9503283, e.g. a compound known as ZM105180, Zemab®, e.g including the dual acting tyrosine kinase inhibitor (ErbB1 and ErbB2) lapatinib (GSK572016), e.g. lapatinib ditosylate; AEE788, panituzumab, trastuzumab (HERCEPTIN®), cetuximab (Erbitux®), geftinib, OSI-774, CI-1033, EKB8569, GW-2016, E1.1, E2.4, E2.5, E6.2, E6.4, E2.11, E6.3 or E7.6.3, 7H-pyrrolo-[2,3-d]pyrimidine derivatives which are e.g. disclosed in WO03013541, erlotinib, vatanalib, gefitinib. Erlotinib can be administered in the form as it is marketed, e.g. TARCEVA®, and gefitinib as IRESSA®, human monoclonal antibodies against the epidermal growth factor receptor including ABX-EGFR.

xxx. an EGFR, PDGFR tyrosine kinase inhibitor; such as EGFR kinase inhibitors, e.g. zalutumumab, tyrphostin 23, tyrphostin 25, tyrphostin 47, tyrphostin 51 and tyrphostin AG 825; 2-propenamide, 2-cyano-3-(3,4-dihydroxyphenyl)-N-phenyl-(2E); tyrphostin Ag 1478; lavendustin A; 3-pyridineacetonitrile, α-[(3,5-dichlorophenyl)methylene]-, (αZ); an example of an EGFR, PDGFR tyrosine kinase inhibitor e.g. includes tyrphostin 46, ZK222584. PDGFR tyrosine kinase inhibitor including tyrphostin 46, SU101. Targets of an EGFR kinase inhibitor include guanylyl cyclase (GC-C) HER2, EGFR, PTK and tubulin.

xxxi. a farnesyltransferase inhibitor; which targets, decreases or inhibits the Ras protein; such as a-hydroxyfarnesylphosphonic acid; butanoic acid, 2-[[(2S)-2-[[(2S,3S)-2-[[(2R)-2-amino-3-mercaptopropyl]amino]-3-methylpentyl]oxy]-1-oxo-3-phenylpropyl]amino]-4-(methylsulfonyl)-, 1-methylethyl ester, (2S); manumycin A; L-744,832 or DK8G557, tipifarnib (R115777), SCH66336 (lonafarnib), BMS-214662, xxxii. a Flk-1 kinase inhibitor; which targets, decreases or inhibits Flk-1 tyrosine kinase activity; such as 2-propenamide, 2-cyano-3-[4-hydroxy-3,5-bis(1-methylethyl) phenyl]-N-(3-phenylpropyl)-(2E). A target of a Flk-1 kinase inhibitor includes, but is not limited to, KDR.

xxxiii. a Glycogen synthase kinase-3 (GSK3) inhibitor; which targets, decreases or inhibits glycogen synthase kinase-3 (GSK3); such as indirubin-3'-monooxime. Glycogen Synthase Kinase-3 (GSK-3; tau protein kinase I), a highly conserved, ubiquitously expressed serine/threonine protein kinase, is involved in the signal transduction cascades of multiple cellular processes. which is a protein kinase that has been shown to be involved in the regulation of a diverse array of cellular functions, including protein synthesis, cell proliferation, cell differentiation, microtubule assembly/disassembly, and apoptosis.

xxxiv. a histone deacetylase (HDAC) inhibitor; which inhibits the histone deacetylase and which possess antiproliferative activity; such as compounds disclosed in WO0222577, especially N-hydroxy-3-[4-[[(2-hydroxyethyl)[2-(1H-indol-3-yl)ethyl]-amino]methyl]phenyl]-2E-2-propenamide, and N-hydroxy-3-[4-[[[2-(2-methyl-1H-indol-3-yl)-ethyl]-amino]methyl]phenyl]-2E-2-propenamide and pharmaceutically acceptable salts thereof; suberoylanilide hydroxamic acid (SAHA); [4-(2-amino-phenylcarbamoyl)-benzyl]-carbamic acid pyridine-3-ylmethyl ester and derivatives thereof; butyric acid, pyroxamide, trichostatin A, oxamflatin, apicidin, depsipeptide (FK228); depudecin; trapoxin, HC toxin, which a cyclic tetrapeptide (cyclo-[prolyl-alanyl-alanyl-2-amino-8-oxo-9,10-epoxydecanoyl]); sodium phenylbutyrate, suberoylanilide hydroxamic acid, suberoyl bis-hydroxamic acid; Trichostatin A, BMS-27275, pyroxamide, FR-901228, valproic acid, PXD101, Savicol®.

xxxv. a HSP90 inhibitor; which targets, decreases or inhibits the intrinsic ATPase activity of HSP90; degrades, targets, decreases or inhibits the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, e.g. a geldanamycin derivative; 17-allylamino-geldanamycin, 17-demethoxygeldanamycin (17AAG), other geldanamycin-related compounds; radicicol and HDAC inhibitors. Other examples of an HSP90 inhibitor include geldanamycin, 17-demethoxy-17-(2-propenylamino). Potential indirect targets of an HSP90 inhibitor include FLT3, BCR-ABL, CHK1, CYP3A5*3 and/or NQ01*2. Nilotinib is an example of an BCR-ABL tyrosine kinase inhibitor.

xxxvi. a I-kappa B-alpha kinase inhibitor (IKK); which targets, decreases or inhibits NF-kappaB, such as 2-propenenitrile, 3-[[(4-methylphenyl)sulfonyl]-(2E).

xxxvii. an insulin receptor tyrosine kinase inhibitor; which modulates the activities of phosphatidylinositol 3-kinase, microtubule-associated protein, and S6 kinases; such as hydroxyl-2-naphthalenylmethylphosphonic acid, LY294002.

xxxviii. a c-Jun N-terminal kinase (JNK) kinase inhibitor; which targets, decreases or inhibits Jun N-terminal kinase; such as pyrazoleanthrone and/or epigallocatechin gallate. Jun N-terminal kinase (JNK), a serine-directed protein kinase, is involved in the phosphorylation and activation of c-Jun and ATF2 and plays a significant role in metabolism, growth, cell differentiation, and apoptosis. A target for a JNK kinase inhibitor includes, but is not limited to, DNMT.

xxxix a microtubule binding agent; which acts by disrupting the microtubular network that is essential for mitotic and interphase cellular function; such as vinca alkaloids, e.g. vinblastine, vinblastine sulfate; vincristine, vincristine sulfate; vindesine; vinorelbine; taxanes, such as taxanes, e.g. docetaxel; paclitaxel; discodermolides; colchicine, epothilones and derivatives thereof, e.g. epothilone B or a derivative thereof. Paclitaxel is marketed as TAXOL®; docetaxel as TAXOTERE®; vinblastine sulfate as VINBLASTIN R.P®; and vincristine sulfate as FARMISTIN®. Also included are the generic forms of paclitaxel as well as various dosage forms of paclitaxel. Generic forms of paclitaxel include, but are not limited to, betaxolol hydrochloride. Various dosage forms of paclitaxel include, but are not limited to albumin nanoparticle paclitaxel marketed as ABRAXANE®; ONXOL®, CYTOTAX®. Discodermolide can be obtained, e.g., as disclosed in U.S. Pat. No. 5,010,099. Also included are Epotholine derivatives which are disclosed in U.S. Pat. No. 6,194,181, WO98/0121, WO9825929, WO9808849, WO9943653, WO9822461 and WO0031247. Especially preferred are Epotholine A and/or B.

xl. a mitogen-activated protein (MAP) kinase-inhibitor; which targets, decreases or inhibits Mitogen-activated protein, such as benzenesulfonamide, N-[2-[[[3-(4-chlorophenyl)-2-propenyl]methyl]amino]methyl]phenyl]-N-(2-hydroxyethyl)-4-methoxy. The mitogen-activated protein (MAP) kinases are a group of protein serine/threonine kinases that are activated in response to a variety of extracellular stimuli and mediate signal transduction from the cell surface to the nucleus. They regulate several physiological and pathological cellular phenomena, including inflammation, apoptotic cell death, oncogenic transformation, tumor cell invasion, and metastasis.

xli. a MDM2 inhibitor; which targets, decreases or inhibits the interaction of MDM2 and the p53 tumor suppressor; such as trans-4-iodo, 4'-boranyl-chalcone.

xlii. a MEK inhibitor; which targets, decreases or inhibits the kinase activity of MAP kinase MEK; such as sorafenib, e.g. Nexavar® (sorafenib tosylate), butanedinitrile, bis[amino[2-aminophenyl)thio]methylene]. A target of a MEK inhibitor includes, but is not limited to ERK. An indirect target of a MEK inhibitor includes, but is not limited to, cyclin D1.

xliii: a matrix metalloproteinase inhibitor (MMP) inhibitor; which targets, decreases or inhibits a class of protease enzyme that selectively catalyze the hydrolysis of polypeptide bonds including the enzymes MMP-2 and MMP-9 that are involved in promoting the loss of tissue structure around tumors and facilitating tumor growth, angiogenesis, and metastasis such as actinonin, which is also known as butanediamide, N-4-hydroxy-N1-[(1S)-1-[[(2S)-2-(hydroxymethyl)-1-pyrrolidinyl]carbonyl]-2-methylpropyl]-2-pentyl-, (2R)-(9Cl); epigallocatechin gallate; collagen peptidomimetic and non-peptidomimetic inhibitors; tetracycline derivatives, e.g., hydroxamate peptidomimetic inhibitor batimastat; and its orally-bioavailable analogue marimastat, prinomastat, metastat, neovastat, tanomastat, TAA211, BMS-279251, BAY 12-9566, MMI270B or AAJ996. A target of a MMP inhibitor includes, but is not limited to, polypeptide deformylase.

xliv. a NGFR tyrosine-kinase-inhibitor; which targets, decreases or inhibits nerve growth factor dependent $p140^{c-trk}$ tyrosine phosphorylation; such as tyrphostin AG 879. Targets of a NGFR tyrosine-kinase-inhibitor include, but are not limited to, HER2, FLK1, FAK, TrkA, and/or TrkC. An indirect target inhibits expression of RAF1.

xlv. a p38 MAP kinase inhibitor, including a SAPK2/p38 kinase inhibitor; which targets, decreases or inhibits p38-MAPK, which is a MAPK family member, such as phenol, 4-[4-(4-fluorophenyl)-5-(4-pyridinyl)-1H-imidazol-2-yl]. An example of a a SAPK2/p38 kinase inhibitor includes, but is not limited to, benzamide, 3-(dimethylamino)-N-[3-[(4-hydroxybenzoyl)amino]-4-methylphenyl]. A MAPK family member is a serine/threonine kinase activated by phosphorylation of tyrosine and threonine residues. This kinase is phosphorylated and activated by many cellular stresses and inflammatory stimuli, thought to be involved in the regulation of important cellular responses such as apoptosis and inflammatory reactions.

xlvi. a p56 tyrosine kinase inhibitor; which targets, decreases or inhibits p56 tyrosine kinase, which is an enzyme that is a lymphoid-specific src family tyrosine kinase critical for T-cell development and activation; such as damnacanthal, which is also known as 2-anthracenecarboxaldehyde, 9,10-dihydro-3-hydroxy-1methoxy-9,10-dioxo, Tyrphostin 46. A target of a p56 tyrosine kinase inhibitor includes, but is not limited to, Lck. Lck is associated with the cytoplasmic domains of CD4, CD8 and the beta-chain of the IL-2 receptor, and is thought to be involved in the earliest steps of TCR-mediated T-cell activation.

xlvii. a PDGFR tyrosine kinase inhibitor; targeting, decreasing or inhibiting the activity of the C-kit receptor tyrosine kinases (part of the PDGFR family), such as targeting, decreasing or inhibiting the activity of the c-Kit receptor tyrosine kinase family, especially inhibiting the c-Kit receptor. Examples of targets of a PDGFR tyrosine kinase inhibitor includes, but are not limited to PDGFR, FLT3 and/or c-KIT; such as tyrphostin AG 1296; tyrphostin 9; 1,3-butadiene-1,1,3-tricarbonitrile, 2-amino-4-(1H-indol-5-yl); N-phenyl-2-pyrimidine-amine derivative, e.g. imatinib, IRESSA®, MLN518. PDGF plays a central role in regulating cell proliferation, chemotaxis, and survival in normal cells as well as in various disease states such as cancer, atherosclerosis, and fibrotic disease. The PDGF family is composed of dimeric isoforms (PDGF-M, PDGF-BB, PDGF-AB, PDGF-CC, and PDGF-DD), which exert their cellular effects by differentially binding to two receptor tyrosine kinases. PDGFR-α and PDGFR-β have molecular masses of ~170 and 180 kDa, respectively.

xlviii. a phosphatidylinositol 3-kinase inhibitor; which targets, decreases or inhibits PI 3-kinase; such as wortmannin, which is also known as 3H-Furo[4,3,2-de]indeno[4,5-h]-2-benzopyran-3,6,9-trione, 11-(acetyloxy)-1,6b,7,8,9a,10,11,11b-octahydro-1-(methoxymethyl)-9a,11b-dimethyl-, (1S,6bR,9aS,11R,11bR)-(9Cl); 8-phenyl-2-(morpholin-4-yl)-chromen-4-one; quercetin, quercetin dihydrate. PI 3-kinase activity has been shown to increase in response to a number of hormonal and growth factor stimuli, including insulin, platelet-derived growth factor, insulin-like growth factor, epidermal growth factor, colony-stimulating factor, and hepatocyte growth factor, and has been implicated in processes related to cellular growth and transformation. An example of a target of a phosphatidylinositol 3-kinase inhibitor includes, but is not limited to, Pi3K.

xlix. a phosphatase inhibitor; which targets, decreases or inhibits phosphatase; such as cantharidic acid; cantharidin; and L-leucinamide, N-[4-(2-carboxyethenyl)benzoyl]glycyl-L-α-glutamyl-(E). Phosphatases remove the phosphoryl group and restore the protein to its original dephosphorylated state. Hence, the phosphorylation-dephosphorylation cycle can be regarded as a molecular "on-off" switch.

l. a platinum agent; which contains platinum and inhibit DNA synthesis by forming interstrand and intrastrand cross-linking of DNA molecules; such as carboplatin; cisplatin; oxaliplatin; cisplatinum; satraplatin and platinum agents such as ZD0473, BBR3464. Carboplatin can be administered, e.g., in the form as it is marketed, e.g. CARBOPLAT®; and oxaliplatin as ELOXATIN®.

li. a protein phosphatase inhibitor, including a PP1 and PP2 inhibitor and a tyrosine phosphatase inhibitor; which targets, decreases or inhibits protein phosphatase. Examples of a PP1 and PP2A inhibitor include cantharidic acid and/or cantharidin. Examples of a tyrosine phosphatase inhibitor include, but are not limited to, L-P-bromotetramisole oxalate; 2(5H furanone, 4-hydroxy-5-hydroxymethyl3-(1-oxohexadecyl)-, (5R); and benzylphosphonic acid.

The term "a PP1 or PP2 inhibitor", as used herein, relates to a compound which targets, decreases or inhibits Ser/Thr protein phosphatases. Type I phosphatases, which include PP1, can be inhibited by two heatstable proteins known as Inhibitor-1 (I-1) and Inhibitor-2 (I-2). They preferentially dephosphorylate a subunit of phosphorylase kinase. Type II phosphatases are subdivided into spontaneously active (PP2A), $CA^{2+}$-dependent (PP2B), and $Mg^{2+}$-dependent (PP2C) classes of phosphatases.

The term "tyrosine phosphatase inhibitor", as used here, relates to a compounds which targets, decreases or inhibits tyrosine phosphatase. Protein tyrosine phosphatases (PTPs) are relatively recent additions to the phosphatase family. They remove phosphate groups from phosphorylated tyrosine residues of proteins. PTPs display diverse structural features and play important roles in the regulation of cell proliferation, differentiation, cell adhesion and motility, and cytoskeletal function. Examples of targets of a tyrosine phosphatase inhibitor include, but are not limited to, alkaline phosphatase (ALP), heparanase, PTPase, and/or prostatic acid phosphatase.

lii. a PKC inhibitor and a PKC delta kinase inhibitor: The term "a PKC inhibitor", as used herein, relates to a compound which targets, decreases or inhibits protein kinase C as well as its isozymes. Protein kinase C (PKC), a ubiquitous, phospholipid-dependent enzyme, is involved in signal transduction associated with cell proliferation, differentiation, and apoptosis. Examples of a target of a PKC inhibitor include, but are not limited to, MAPK and/or NF-kappaB. Examples of a PKC inhibitor include, but are not limited to, 1-H-pyrrolo-2,5-dione, 3-[1-[3-(dimethylamino)propyl]-1H-indol-3-yl]-4-(1H-indol-3-yl); bisindolylmaleimide IX; sphingosine, which is known as 4-octadecene-1,3-diol, 2-amino-, (2S,3R,4E)-(9Cl); staurosporine, which is known as 9,13-Epoxy-1H,9H-diindolo[1,2,3-gh:3',2', 1'-lm]pyrrolo[3,4-j][1,7]benzodiazonin-1-one, staurosporine derivatives such as disclosed in EP0296110, e.g. midostaurin; 2,3,10,11,12,13-hexahydro-10-methoxy-9-methyl-11-(methylamino)-, (9S,10R,11R,13R)-(9Cl); tyrphostin 51; hypericin, which is also known as phenanthro[1,10,9,8-opqra]perylene-7,14-dione, 1,3,4,6,8,13-hexahydroxy-10,11-dimethyl-, enzastaurin (LY317615)stereoisomer, UCN-01, safingol, BAY 43-9006, bryostatin 1, perifosine; llmofosine; RO 318220 and RO 320432; GO 6976; Isis 3521; LY333531/LY379196. The term "a PKC delta kinase inhibitor", as used herein, relates to a compound which targets, decreases or inhibits the delta isozymes of PKC. The delta isozyme is a conventional PKC isozymes and is $Ca^{2+}$-dependent. An example of a PKC delta kinase inhibitor includes, but is not limited to, Rottlerin, which is also known as 2-Propen-1-one, 1-[6-[(3-acetyl-2,4,6-trihydroxy-5-methylphenyl)methyl]-5,7-dihydroxy-2,2-dimethyl-2H-1-benzopyran-8-yl]-3-phenyl-, (2E).

liii. a polyamine synthesis inhibitor; which targets, decreases or inhibits polyamines spermidine; such as DMFO, which is also known as (−)-2-difluoromethylornithin; N1, N12-diethylspermine 4HCl. The polyamines spermidine and spermine are of vital importance for cell proliferation, although their precise mechanism of action is unclear. Tumor cells have an altered polyamine homeostasis reflected by increased activity of biosynthetic enzymes and elevated polyamine pools.

liv. a proteosome inhibitor; which targets, decreases or inhibits proteasome, such as aclacinomycin A; gliotoxin; PS-341; MLN 341; bortezomib; velcade. Examples of targets of a proteosome inhibitor include, but are not limited to, O(2)(−)-generating NADPH oxidase, NF-kappaB, and/or farnesyltransferase, geranyltransferase I.

lv. a PTP1 B inhibitor; which targets, decreases or inhibits PTP1B, a protein tyrosine kinase inhibitor; such as L-leucinamide, N-[4-(2-carboxyethenyl)benzoyl]glycyl-L-α-glutamyl-, (E).

lvi. a protein tyrosine kinase inhibitor including a SRC family tyrosine kinase inhibitor; a Syk tyrosine kinase inhibitor; and a JAK-2 and/or JAK-3 tyrosine kinase inhibitor; The term "a protein tyrosine kinase inhibitor", as used herein, relates to a compound which which targets, decreases or inhibits protein tyrosine kinases. Protein tyrosine kinases (PTKs) play a key role in the regulation of cell proliferation, differentiation, metabolism, migration, and survival. They are classified as receptor PTKs and non-receptor PTKs. Receptor PTKs contain a single polypeptide chain with a transmembrane segment. The extracellular end of this segment contains a high affinity ligand-binding domain, while the cytoplasmic end comprises the catalytic core and the regulatory sequences. Examples of targets of a tyrosine kinase inhibitor include, but are not limited to, ERK1, ERK2, Bruton's tyrosine kinase (Btk), JAK2, ERK ½, PDGFR, and/or FLT3. Examples of indirect targets include, but are not limited to, TNFalpha, NO, PGE2, IRAK, iNOS, ICAM-1, and/or E-selectin. Examples of a tyrosine kinase inhibitor include, but are not limited to, tyrphostin AG 126; tyrphostin Ag 1288; tyrphostin Ag 1295; geldanamycin; and genistein.

Non-receptor tyrosine kinases include members of the Src, Tec, JAK, Fes, Abl, FAK, Csk, and Syk families. They are located in the cytoplasm as well as in the nucleus. They exhibit distinct kinase regulation, substrate phosphorylation, and function. Deregulation of these kinases has also been linked to several human diseases. The term "a SRC family tyrosine kinase inhibitor", as used herein, relates to a compound which which targets, decreases or inhibits SRC. Examples of a SRC family tyrosine kinase inhibitor include, but are not limited to, PP1, which is also known as 1H-pyrazolo[3,4-d]pyrimidin-4-amine, 1-(1,1-dimethylethyl)-3-(1-naphthalenyl); and PP2, which is also known as 1H-Pyrazolo[3,4-d]pyrimidin-4-amine, 3-(4-chlorophenyl)-1-(1,1-dimethylethyl).

The term "a Syk tyrosine kinase inhibitor", as used herein, relates to a compound which targets, decreases or inhibits Syk. Examples of targets for a Syk tyrosine kinase inhibitor include, but are not limited to, Syk, STAT3, and/or STAT5. An example of a Syk tyrosine kinase inhibitor includes, but is not limited to, piceatannol, which is also known as 1,2-benzenediol, 4-[(1E)-2-(3,5-dihydroxyphenyl)ethenyl].

The term "a Janus (JAK-2 and/or JAK-3) tyrosine kinase inhibitor", as used herein, relates to a compound which targets, decreases or inhibits janus tyrosine kinase. Janus tyrosine kinase inhibitor are shown anti-leukemic agents with anti-thrombotic, anti-allergic and immunosuppressive properties. Targets of a JAK-2 and/or JAK-3 tyrosine kinase inhibitor include, but are not limited to, JAK2, JAK3, STAT3. An indirect target of an JAK-2 and/or JAK-3 tyrosine kinase inhibitor includes, but is not limited to CDK2. Examples of a JAK-2 and/or JAK-3 tyrosine kinase inhibitor include, but are not limited to, Tyrphostin AG 490; and 2-naphthyl vinyl ketone.

Compounds which target, decrease or inhibit the activity of c-Abl family members and their gene fusion products, e.g. include PD180970; AG957; or NSC 680410.

lvii. a retinoid; which target, decrease or inhibit retinoid dependent receptors; such as isotretinoin, tretinoin, alitretinoin, bexarotene, e.g. including an agent which interact with retinoic acid responsive elements on DNA, such as isotretinoin (13-cis-retinoic acid).

lviii. a RNA polymerase II elongation inhibitor; which targets, decreases or inhibits insulin-stimulated nuclear and cytosolic p70S6 kinase in CHO cells; targets, decreases or inhibits RNA polymerase II transcription, which may be dependent on casein kinase II; and targets, decreases or inhibits germinal vesicle breakdown in bovine oocytes; such as 5,6-dichloro-1-beta-D-ribofuranosylbenzimidazole.

lix. a serine/threonine kinase inhibitor; which inhibits serine/threonine kinases; such as 2-aminopurine. An example of a target of a serine/threonine kinase inhibitor includes, but is not limited to, dsRNA-dependent protein kinase (PKR). Examples of indirect targets of a serine/threonine kinase inhibitor include, but are not limited to, MCP-1, NF-kappaB, eIF2alpha, COX2, RANTES, IL8, CYP2A5, IGF-1, CYP2B1, CYP2B2, CYP2H1, ALAS-1, HIF-1, erythropoietin, and/or CYP1A1.

lx. a sterol biosynthesis inhibitor; which inhibits the biosynthesis of sterols such as cholesterol; such as terbinadine. Examples of targets for a sterol biosynthesis inhibitor include, but are not limited to, squalene epoxidase, and CYP2D6. An example of a sterol biosynthesis inhibitor includes, but is not limited to, terbinadine.

lxi. a topoisomerase inhibitor; including a topoisomerase I inhibitor and a topoisomerase II inhibitor. Examples of a topoisomerase I inhibitor include, but are not limited to, topotecan, gimatecan, irinotecan, camptothecan and its analogues, 9-nitrocamptothecin and the macromolecular camptothecin conjugate PNU-166148 (compound A1 in WO9917804); 10-hydroxycamptothecin e.g. the acetate salt; idarubicin, e.g. the hydrochloride; irinotecan, e.g. the hydrochloride; etoposide; teniposide; topotecan, topotecan hydrochloride; doxorubicin; epirubicin, epirubicin hydrochloride; 4'-epidoxorubicin, mitoxantrone, mitoxantrone, e.g. the hydrochloride; daunorubicin, daunorubicin hydrochloride, valrubicin, dasatinib (BMS-354825). Irinotecan can be administered, e.g., in the form as it is marketed, e.g., under the trademark CAMPTOSAR®. Topotecan can be administered, e.g., in the form as it is marketed, e.g., under the trademark HYCAMTIN®. The term "topoisomerase II inhibitor", as used herein, includes, but is not limited to, the anthracyclines, such as doxorubicin, including liposomal formulation, e.g., CAELYX®, daunorubicin, including liposomal formulation, e.g., DAUNOSOME®, epirubicin, idarubicin and nemorubicin; the anthraquinones mitoxantrone and losoxantrone; and the podophillotoxines etoposide and teniposide. Etoposide is marketed as ETOPOPHOS®; teniposide as VM 26-BRISTOL®; doxorubicin as ADRIBLASTIN® or ADRIAMYCIN®; epirubicin as FARMORUBICIN® idarubicin as ZAVEDOS®; and mitoxantrone as NOVANTRON®.

lxii. VEGFR tyrosine kinase inhibitor; which targets, decreases and/or inhibits the known angiogenic growth factors and cytokines implicated in the modulation of normal and pathological angiogenesis. The VEGF family (VEGF-A, VEGF-B, VEGF-C, VEGF-D) and their corresponding receptor tyrosine kinases [VEGFR-1 (Flt-1), VEGFR-2 (Flk-1, KDR), and VEGFR-3 (Flt-4)] play a paramount and indispensable role in regulating the multiple facets of the angiogenic and lymphangiogenic processes. An example of a VEGFR tyrosine kinase inhibitor includes 3-(4-dimethylaminobenzylidenyl)-2-indolinone. Compounds which target, decrease or inhibit the activity of VEGFR are especially compounds, proteins or antibodies which inhibit the VEGF receptor tyrosine kinase, inhibit a VEGF receptor or bind to VEGF, and are in particular those compounds, proteins or monoclonal antibodies generically and specifically disclosed in WO9835958, e.g.1-(4-chloroanilino)-4-(4-pyridylmethyl)phthalazine or a pharmaceutical acceptable salt thereof, e.g. the succinate, or in WO0009495, WO0027820, WO0059509, WO9811223, WO0027819 and EP0769947; e.g. those as described by M. Prewett et al in Cancer Research 59 (1999) 5209-5218, by F. Yuan et al in Proc. Natl. Acad. Sci. USA, vol. 93, pp. 14765-14770, Dec. 1996, by Z. Zhu et al in Cancer Res. 58, 1998, 3209-3214, and by J. Mordenti et al in Toxicologic Pathology, Vol. 27, no. 1, pp 14-21, 1999; in WO0037502 and WO9410202; Angiostatin, described by M. S. O'Reilly et al, Cell 79,1994,315328; Endostatin described by M. S. O'Reilly et al, Cell 88, 1997, 277-285; anthranilic acid amides; ZD4190; ZD6474 (vandetanib); SU5416; SU6668, AZD2171 (Recentin®); or anti-VEGF antibodies, such as anti-VEGF-alpha antibody tanibizumab (Lucentis®), or anti-VEGF receptor antibodies, e.g. RhuMab (bevacizumab, Avastin®). By antibody is meant intact monoclonal antibodies, polyclonal antibodies, multispecific antibodies formed from at least 2 intact antibodies, and antibodies fragments so long as they exhibit the desired biological activity. an example of an VEGF-R2 inhibitor e.g. includes axitinib, lxiii. a gonadorelin agonist, such as abarelix, goserelin, goserelin acetate, lxiv. a compound which induce cell differentiation processes, such as retinoic acid, alpha-, gamma- or 8-tocopherol or alpha-, gamma- or 8-tocotrienol.

lxv. a bisphosphonate, e.g. including etridonic, clodronic, tiludronic, pamidronic, alendronic, ibandronic, risedronic and zoledronic acid.

lxvi. a heparanase inhibitor which prevents heparan sulphate degradation, e.g. PI-88, lxvii. a biological response modifier, preferably a lymphokine or interferons, e.g. interferon alpha, lxviii. a telomerase inhibitor, e.g. telomestatin, lxix. mediators, such as inhibitors of catechol-O-methyltransferase, e.g. entacapone, lxx: inhibitors of Kinesin Spindle Protein (KSP), such as ispinesib, lxxi somatostatin or a somatostatin analogue, such as octreotide (Sandostatin® or Sandostatin LAR®).

lxxii. Growth Hormone-Receptor Antagonists, such as pegvisomant, filgrastim or pegfilgrastim, or interferon alpha:

lxxiii. monoclonal antibodies, e.g. useful for leukemia (AML) treatment, such as alemtuzumab (Campath®), gemtuzumab, (ozogamicin, Mylotarg®), epratuzumab.

lxxiv. cytoxic antineoplastics, e.g. including altretamine, amsacrine, asparaginase (Elspar®), pegaspargase (PEG-L-asparaginase, Oncaspar®)), denileukin diftitox (Ontak®)), masoprocol, lxxv. a phosphodiesterase inhibitor, e.g. anagrelide (Agrylin®, Xagrid®)).

lxxvi. a cancer vaccine, such as MDX-1379.
lxxvii. an immunosuppressive monoclonal antibody, e.g., monoclonal antibodies to leukocyte receptors or their ligands,
  e.g. CD20, such as rituximab (Rituxan®), ibritumomab tiuxetan conjugated to $^{111}$In or $^{90}$Y (Zevalin®), $^{131}$I tositumumab ( )Bexxar®), ofatumumab (HuMax-CD20(R)), ocrelizumab, hA20 (Immunomedics),
  CD22, such as epratuzumab, inotizumab ozogamicin (CMC544), CAT-3888,
  CD33, such as gemtuzumab (Mylotarg®,
  CD52, e.g. alemtuzumab (Campath-I®),
    CD11a, e.g. efalizumab (Raptiva®),
  CD3, e.g. visilizumab,
lxxviii. antibodies against carcinoembryonic antigen (CEA), e.g. lapetuzumab, e.g. I apetuzumab-yttrium90, KSB-303, MFECP1, MFE-23,
lxxix. mediators, e.g. inhibitors, of multiple receptor tyrosine kinases associated with tumour growth and angiogenesis, such as sunitinib (SU11248),
lxxx. synthetic nonsteroidal estrogens, e.g. including diethylstilbestrol (DES, Stilboestrol®)),
lxxxi. a recombinant binding molecule having at least a portion of the extracellular domain of CTLA4 or a mutant thereof, or an anti-CLA4 agent" e.g. including an at least extracellular portion of CTLA4 or a mutant thereof joined to a non-CTLA4 protein sequence, such as CTLA4Ig, (e.g. designated ATCC 68629) or a mutant thereof includes but is not limited to LEA29Y (belatacept); an anti-CTLA4 agent includes but is not limited to ipilimumab, ticilimumab.
lxxxii. an alphaVbeta3 and alphaVbeta5 integrin receptor inhibitor, e.g. cilengitide (EMD121974)

Cancer treatment, optionally in combination with an anticancer drug may be associated with radiotherapy, e.g. including DOTATATE therapy, such as $Y^{90}$-DOTATATE therapy. Cancer treatment may also be associated with vitamin or vitamin derivative (e.g. Leucovorin®) treatment.

Anti-cancer drugs e.g. may be used in combination with Abraxane® which may improve the release of drugs, and even may enhance the drug benefit.

If the compounds of the present invention are administered in combination with other drugs dosages of the co-administered second drug will of course vary depending on the type of co-drug employed, on the specific drug employed, on the condition being treated, as in case of a compound of the present invention. In general dosages similar than those as provided by the second drug supplier may be appropriate The chemical names of the compounds of the present invention as indicated herein are copied from ISIS, version 2.5 (AutoNom 2000 Name).

Whenever patent applications are cited herein, the content thereof is, particularly the chemical compounds indicated therein are, introduced herein by reference.

In the following Examples all temperatures indicated are in degree Celsius (° C.).

The following abbreviations are used
DABCO 1,4-diaza-bicyclo[2,2,2]octane
DIEA Diisopropylethyl amine
DMF N,N-dimethylformamide
EDC N-Ethyl, N'-(3-dimethylaminopropyl)-carbodiimide
ETOH ethyl alcohol
EtOAc Ethyl acetate
HOAt 1-Hydroxy-7-aza-1,2,3-benzotriazole
LiHMDS lithium hexamethyldisilazide
rt Room temperature
TBME t.butyl-methylether
TFA trifluoroacetic acid
THF tertahydrofurane
TMSI trimethylsilyliodide

PREPARATION EXAMPLE 1

4'-Octyloxy-biphenyl-4-carboxylic acid [3-(1,1,4-trioxo-1,2,5-thiadiazolidin-2-yl)-phenyl]-amide (Compound of Example 1 in TABLE 1 Below)

A) (3-Nitro-phenylamino)-acetic acid ethyl ester

To 14.2 mmol of 3-nitronaniline dissolved in 50 ml of DMF are added 35.5 mmol of $K_2CO_3$, 18-crown-6 in catalytic amount and 14.2 mmol of bromo acetic acid and the mixture obtained is stirred for 22 hours at 60°. The mixture obtained is diluted with EtOAc and extracted with water and with 1N HCl. The organic layer obtained is dried and solvent is evaporated. (3-Nitro-phenylamino)-acetic acid ethyl ester is obtained.

B) (3-Nitro-phenyl-N-(t-butylaminosulfonyl)amino)-acetic acid ethyl ester

To a mixture of 25.7 mmol tert.butanol and 20 ml of $CH_2Cl_2$ are added 10.3 mmol of $ClSO_2NCO$ and the mixture obtained is stirred at rt for 45 minutes. The mixture obtained is slowly added to a solution of 5.14 mmol of (3-nitro-phenylamino)-acetic acid ethyl ester and 15.4 mmol of triethylamine in 50 ml of $CH_2Cl_2$ at 0° and the mixture obtained is stirred at 0° for 2.5 hours. The mixture obtained is diluted with $CH_2Cl_2$ and the dilution is extracted with HCl (0.1N). The organic layer obtained is dried, and solvent is evaporated. (3-Nitro-phenyl-N-(t-butylaminosulfonyl)amino)-acetic acid ethyl ester is obtained.

C) (3-Nitro-phenyl-N-(aminosulfonyl)amino)-acetic acid ethyl ester in the form of a trifluoroacetate 5 mmol of (3-nitro-phenyl-N-(t-butylaminosulfonyl)amino)-acetic acid ethyl ester is dissolved in 20 ml of 90% aqueous TFA and the mixture obtained is stirred for 1 hour at rt. The mixture obtained is diluted with dioxane and solvent is evaporated. (3-Nitro-phenyl-N-(aminosulfonyl)amino)-acetic acid ethyl ester in the form of a trifluoroacetate is obtained.

D) 5-(3-Nitro-phenyl)-1,1-dioxo-1,2,5-thiadiazolidin-3-one 4.56 mmol of (3-nitro-phenyl-N-(aminosulfonyl)amino)-acetic acid ethyl ester in the form of a trifluoroacetate is dissolved in 50 ml of THF, to the mixture obtained 13.7 mmol of $NaN[Si(CH_3)_3]_2$ are added and the mixture obtained is stirred at rt under argon for 1.5 hours. The mixture obtained is diluted with EtOAc, the dilution obtained is extracted with a 1:1 mixture of 1M HCl and brine, the organic layer obtained is dried and solvent is evaporated. 5-(3-Nitro-phenyl)-1,1-dioxo-1,2,5-thiadiazolidin-3-one is obtained.

E) 5-(3-Amino-phenyl)-1,1-dioxo-1,2,5-thiadiazolidin-3-one 3.32 mmol of 5-(3-nitro-phenyl)-1,1-dioxo-1,2,5-thiadiazolidin-3-one are dissolved in methanol, to the mixture obtained 1.18 mmol of Pd/C are added and the reaction flask is fitted with a $H_2$-balloon. The reaction mixture is stirred under H$_2$-atmosphere for 5 hours. From the mixture obtained the catalyst is removed by filtration. From the filtrate solvent is evaporated. 5-(3-Amino-phenyl)-1,1-dioxo-1,2,5-thiadiazolidin-3-one is obtained.

F) 4'-Octyloxy-biphenyl-4-carboxylic acid [3-(1,1,4-trioxo-1,2,5-thiadiazolidin-2-yl)-phenyl]-amide 1.06 mmol of 4'-(octyloxy)-4-biphenyl-carboxylic acid, 1.06 mmol of EDC and 1.06 mmol DIPEA are added to a mixture of 0.53 mmol of 5-(3-amino-phenyl)-1,1-dioxo-1,2,5-thiadiazolidin-3-one and 0.11 mmol of HOAt in 6 ml of a DMF/toluene-mixture. The mixture obtained is stirred at rt for 18 hours, diluted with EtOAc and toluene and a precipitate is obtained and filtered off. 4'-Octyloxy-biphenyl-4-carboxylic acid [3-(1,1,4-trioxo-1,2,5-thiadiazolidin-2-yl)phenyl]-amide in solid form is obtained. The filtrate obtained is washed with HCl (1M) and brine, the organic layer is dried and solvent is evaporated. Further 4'-octyloxy-biphenyl-4-carboxylic acid [3-(1,1,4-trioxo-1,2,5-thiadiazolidin-2-yl)-phenyl]-amide is obtained.

PREPARATION EXAMPLE 2

{2-[(4'-Octyloxy-biphenyl-4-carbonyl)-amino]-benzyl}-phosphonic acid (Compound of Example 2 in TABLE 1 Below)

A) (2-Nitro-benzyl)-phosphonic acid diethyl ester

A mixture of 1.02 g of nitrobenzylbromide and 1.08 ml of triethylphosphite in 10 ml of toluene is heated to reflux for 12 hours. From the mixture obtained solvent is evaporated. (2-Nitro-benzyl)-phosphonic acid diethyl ester is obtained.

B) (2-Amino-benzyl)-phosphonic acid diethyl ester 1.13 g of (2-nitro-benzyl)-phosphonic acid diethyl ester) in ethanol are hydrogenated with Pd—C as a catalyst for 5 hours at rt and ambient pressure. The catalyst is removed by filtration and from the filtrate obtained solvent is evaporated. (2-Amino-benzyl)-phosphonic acid diethyl ester is obtained.

C) {2-[(4'-Octyloxy-biphenyl-4-carbonyl)-amino]-benzyl}-phosphonic acid diethylester 1 g of (2-amino-benzyl)-phosphonic acid diethyl ester, 2 g of 4'-octyloxy-biphenyl-4-carboxylic acid, 1.4 ml of EDC, 0.9 ml of DIEA and 100 mg of HOAt are dissolved in 30 ml of DMF and the mixture obtained is stirred at rt for 2 days. The mixture obtained is diluted with EtOAc and the solution obtained is washed with aqueous diluted HCl and aqueous NaHCO$_3$ solution. The organic layer obtained is dried and solvent is evaporated. {2-[(4'-Octyloxy-biphenyl-4-carbonyl)-amino]-benzyl}-phosphonic acid diethylester is obtained in crystalline form and is recrystallized from isopropanol/water.

D) {2-[(4'-Octyloxy-biphenyl-4-carbonyl)-amino]-benzyl}-phosphonic acid

{2-[(4'-Octyloxy-biphenyl-4-carbonyl)-amino]-benzyl}-phosphonic acid diethylester is dissolved in CH$_2$Cl$_2$ and and the mixture obtained is treated with trimethylsilyl iodide at 0°. The mixture obtained is stirred at 0° for several hours and diluted with toluene. From the mixture obtained solvent is evaporated. The evaporation residue obtained is dissolved in 1N NaOH solution, washed with EtOAc, HCl is added, precipitation occurs and the precipitate obtained is collected. {2-[(4'-Octyloxy-biphenyl-4-carbonyl)-amino]-benzyl}-phosphonic acid is obtained.

PREPARATION EXAMPLE 3

{2-[(4'-Benzyloxy-biphenyl-4-carbonyl)-amino]-benzyl}-phosphonic acid ((Compound of Example 31 in TABLE 1 Below) and {2-[(4'-Hydroxy-biphenyl-4-carbonyl)-amino]-benzyl}-phosphonic acid (Compound of Example 32 in TABLE 1 Below)

10 mg of [2-(4-bromo-benzoylamino)-benzyl]-phosphonic acid and 1.4 equivalents of 4-benzyloxybenzeneboronic acid are suspended in DMF/water 1:1, K$_2$CO$_3$ and 1.4 equivalents of catalyst (Pd(OAc)$_2$) are added and the mixture obtained is heated by microwave irradiation to 150° C. for 10 minutes. The mixture obtained is diluted with aqueous ammonia, applied on a C-18 RP cartridge and eluted stepwise with an NH$_4$OH (0.1%)/MeOH gradient. 2-[(4'-Benzyloxy-biphenyl-4-carbonyl)-amino]-benzyl}-phosphonic acid and {2-[(4'-Hydroxy-biphenyl-4-carbonyl)-amino]-benzyl}-phosphonic acid are obtained in the form of ammonium salts.

PREPARATION EXAMPLE 4

[2-({2-[(4'-Hexyl-biphenyl-4-carbonyl)-amino]-benzyl}-hydroxy-phosphinoyloxy)-ethyl]-trimethyl-ammonium, inner salt (Compound of Example 36 in TABLE 1 Below)

40 mg of {2-[(4'-Hexyl-biphenyl-4-carbonyl)-amino]-benzyl}-phosphonic acid (compound of preparation example 3) are dissolved in 10 ml of pyridine and 111 mg of dry choline p-toluolsulfonate salt and 2 ml trichloroacetonitrile are added. The mixture obtained is stirred at 50° C. for 76 hours. From the mixture obtained solvent is evaporated and the evaporation residue is subjected to RP-18 chromatography (0.1% TFA-water/methanol gradient). [2-({2-[(4'-Hexyl-biphenyl-4-carbonyl)-amino]-benzyl}-hydroxy-phosphinoyloxy)-ethyl]-trimethyl-ammonium, inner salt is obtained.

PREPARATION EXAMPLE 5

2,2-Dimethyl-propionic acid hydroxy-{2-[(4'-octyloxy-biphenyl-4-carbonyl)-amino]-benzyl}-phosphinoyloxymethyl ester (Compound of Example 40 in TABLE 1 Below)

50 mg of {2-[(4'-octyloxy-biphenyl-4-carbonyl)-amino]-benzyl}-phosphonic acid (compound of preparation example 2) are suspended in 10 ml of DMF and to the suspension obtained 145 μL chloromethyl pivalate and 70 μL triethylamine and a catalytic amount of sodium iodide are added. The mixture obtained is heated to 65° C. for 24 hours and additional chloromethyl pivalate and triethylamine (20 equivalents each) are added. The mixture obtained is heated for additional 46 hours. The mixture obtained is diluted with DCM and extracted with HCl (0.1M), NaHCO$_3$ (5%) and water (addition of n-butanol). From the organic phase obtained solvent is evaporated. 2,2-Dimethyl-propionic acid hydroxy-{2-[(4'-octyloxy-biphenyl-4-carbonyl)-amino]-benzyl}-phosphinoyloxymethyl ester is obtained in the form of a colorless solid.

PREPARATION EXAMPLE 6

(Difluoro-{4-[(4'-octyloxy-biphenyl-4-carbonyl)-(4-octyloxy-biphenyl-4-carbonyloxy)-amino]-phenyl}-methyl)-phosphonic acid diethyl ester (Compound of Example 41 in TABLE 1 Below) and (Difluoro-{4-[(4'-octyloxy-biphenyl-4-carbonyl)-amino]-phenyl}-methyl)-phosphonic acid diethyl ester (Compound of Example 11 in TABLE 1 Below)

A solution of [difluoro-(4-nitro-phenyl)-methyl]-phosphonic acid diethyl ester in ETOAc is hydrogenated over 10 w/w % palladium on charcoal. From the mixture obtained Pd/C is filtered of and the filtrate obtained is evaporated to dryness. The oil obtained is re-dissolved in $CH_2Cl_2$ and treated with 5 equivalents of pyridine and 1 equivalent of 4'-octyloxy-biphenyl-4-carbonylchloride under stirring. To the mixture obtained EtOAc is added and and the mixture obtained is extracted with $NaHCO_3$. From the organic phase obtained solvent is evaporated and the evaporation residue is subjected to column chromatography. (Difluoro-{4-[(4'-octyloxy-biphenyl-4-carbonyl)-(4'-octyloxy-biphenyl-4-carbonyloxy)-amino]-phenyl}-methyl)-phosphonic acid diethyl ester and (difluoro-{4-[(4'-octyloxy-biphenyl-4-carbonyl)-amino]-phenyl}-methyl)-phosphonic acid diethyl ester are obtained in the form of colourless powders.

PREPARATION EXAMPLE 7

(Difluoro-{2-[(4'-octyloxy-biphenyl-4-carbonyl)-amino]-phenyl}-methyl)-phosphonic acid diethyl ester (Compound of Example 9 in TABLE 1 Below)

Tto a solution of [(2-amino-phenyl)-difluoro-methyl]-phosphonic acid diethyl ester NVP-VAV664 in $CH_2Cl_2$ are added 5 equivalents of pyridine followed by 1 equivalent of 4'-octyloxy-biphenyl-4-carbonylchloride at rt and the mixture obtained is stirred for ca. 10 to 20 minutes. To the mixture obtained EtOAc is added and and the mixture obtained is extracted with $NaHCO_3$. From the organic phase obtained solvent is evaporated and the evaporation residue is subjected to column chromatography. (Difluoro-{2-[(4'-octyloxy-biphenyl-4-carbonyl)-amino]-phenyl}-methyl)-phosphonic acid diethyl ester is obtained in the form of a colourless powder.

PREPARATION EXAMPLE 8

(Difluoro-{2-[(4'-octyloxy-biphenyl-4-carbonyl)-amino]-phenyl}-methyl)-phosphonic acid ethyl ester methyl ester (Compound of Example 37 in TABLE 1 Below), (Difluoro-{2-[methyl-(4'-octyloxy-biphenyl-4-carbonyl)-amino]-phenyl}-methyl)-phosphonic acid diethyl ester (Compound of Example 55 in TABLE 2 Below), and (Difluoro-{2-[methyl-(4'-octyloxy-biphenyl-4-carbonyl)-amino]-phenyl}-methyl)-phosphonic acid ethyl ester methyl ester (Compound of Example 56 in TABLE 2 Below)

At rt 0.5 ml 1M LiHMDS in THF are added to a solution of 200 mg of (difluoro-{2-[(4'-octyloxy-biphenyl-4-carbonyl)-amino]-phenyl}-methyl)-phosphonic acid diethyl ester and to the mixture obtained 0.1 ml of methyliodide in 30 ml of THF are added. The mixture obtained is stirred for 3 hours at rt and partitiond between ETOAc and 1N aquueous HCl. The organic phase is separated and dried and an etheral solution of diazomethane is added until the characteristic yellow colour remains. Solvent is evaporated and the evaporation residue is subjected to chromatography.

(Difluoro-{2-[(4'-octyloxy-biphenyl-4-carbonyl)-amino]-phenyl}-methyl)-phosphonic acid ethyl ester methyl ester, (difluoro-{2-[methyl-(4'-octyloxy-biphenyl-4-carbonyl)-amino]-phenyl}-methyl)-phosphonic acid diethyl ester and (difluoro-{2-[methyl-(4'-octyloxy-biphenyl-4-carbonyl)-amino]-phenyl}-methyl)-phosphonic acid ethyl ester methyl ester are obtained in the form of colourless powders.

PREPARATION EXAMPLE 9

(Difluoro-{2-[(4'-octyloxy-biphenyl-4-carbonyl)-amino]-phenyl}-methyl)-phosphonic acid monoethyl ester (Compound of Example 12 in TABLE 1 Below)

To a solution of (difluoro-{2-[(4'-octyloxy-biphenyl-4-carbonyl)-amino]-phenyl}-methyl)-phosphonic acid diethyl ester in THF are added, at rt, 1.5 equivalents of LiHMDS and the mixture obtained is stirred at rt for ca. 24 hours. The mixture obtained is partitioned between EtOAc and 1N-aqueous HCl, the organic phase obtained is washed with 1N aqueous HCl, separated and evaporated to dryness. The evaporation residue obtained is subjected to reversed phase chromatography (RP-18). (Difluoro-{2-[(4'-octyloxy-biphenyl-4-carbonyl)-amino]-phenyl}-methyl)-phosphonic acid monoethyl ester is obtained in the form of a slightly yellow powder.

PREPARATION EXAMPLE 10

(Difluoro-{4-[(4'-octyloxy-biphenyl-4-carbonyl)-amino]-phenyl}-methyl)-phosphonic acid monoethyl ester (Compound of Example 14 in TABLE 1 Below)

A solution of (difluoro-{4-[(4'-octyloxy-biphenyl-4-carbonyl)-amino]-phenyl}-methyl)-phosphonic acid diethyl ester and aproximately 5 to 7 equivalents NaI in acetone/acetonitrile is heated to 150° C. in a microwave reactor for less then 40 minutes. The mixture obtained is partitioned between EtOAc and 1N aqueous HCl, the organic phase obtained is washed with 1N aqueous HCl, separated and evaporated to dryness.

(Difluoro-{4-[(4'-octyloxy-biphenyl-4-carbonyl)-amino]-phenyl}-methyl)-phosphonic acid monoethyl ester is obtained.

PREPARATION EXAMPLE 11

(Difluoro-{3-[methyl-(4'-octyloxy-biphenyl-4-carbonyl)-amino]-phenyl}-methyl)-phosphonic acid monoethyl ester (Compound of Example 61 in TABLE 2 Below)

A solution of (difluoro-{3-[methyl-(4'-octyloxy-biphenyl-4-carbonyl)-amino]-phenyl}-methyl)-phosphonic acid diethyl ester (compound of example 59 in TABLE 2 below) and approximately 3 to 5 equivalents of DABCO in acetonitrile solution is heated to 150° C. in a microwave reactor for less then 40 minutes. The mixture obtained is partitioned between EtOAc and 1N aqueous HCl. From the mixture obtained the organic phase is separated, washed with 1N aqueous HCl, and evaporated to dryness. (Difluoro-{3-[methyl-(4'-octyloxy-biphenyl-4-carbonyl)-amino]-phenyl}-methyl)-phosphonic acid monoethyl ester is obtained.

PREPARATION EXAMPLE 12

(Difluoro-{4-[methyl-(4-octyloxy-biphenyl-4-carbonyl)-amino]-phenyl}-methyl)-phosphonic acid (Compound of Example 62 in TABLE 2 Below)

To a cooled (0 to 5° C.) solution of 43 mg of (difluoro-{4-[methyl-(4'-octyloxy-biphenyl-4-carbonyl)-amino]-phenyl}-methyl)-phosphonic acid ethyl ester methyl ester (compound of example 58 in TABLE 2), in 4 ml of $CH_2Cl_2$ are added 9 equivalents of TMSI and the mixture obtained is stirred at 0 to 5° C. until TLC indicated completion of the reaction. The mixture obtained is partitioned between 1N aqueous HCl and EtOAc, the organic layer is separated, dried and solvent is evaporated. The evaporation residue obtained is re-suspended in EtOAc and again solvent is evaporated and the latter procedure is repeated several times in order to remove impurities originating from TMSI.
(Difluoro-{4-[methyl-(4'-octyloxy-biphenyl-4-carbonyl)-amino]-phenyl}-methyl)-phosphonic acid is obtained in the form of a colourless solid.

PREPARATION EXAMPLE 13

(2-{2-[(4'-Octyloxy-biphenyl-4-carbonyl)-amino]-phenyl}-ethyl)-phosphonic acid diethyl ester (Compound of Example 47 in TABLE 1 Below)

158 mg of (2-nitro-phenylethynyl)-phosphonic acid diethyl ester are hydrogenated at rt in 15 ml of EtOH over 10 w/w % palladium on charcoal. From the mixture obtained the catalyst is filtered off and, from the filtrate obtained solvent is evaporated to dryness. A slightly orange coloured oil is obtained and dissolved in 15 ml of EtOAc and 0.3 ml of pyridine. To the mixture obtained 190 mg of 4'-n-octyloxy-biphenyl-carbonylchloride are added and the reaction mixture is stirred. For work-up, the mixture obtained is partitioned between aqueqous saturated $NaHCO_3$-solution and EtOAc, the organic layer is separated and washed with brine, 1N aquesous HCl and brine, dried, and from the dried solution solvent is evaporated at reduced pressure. A solid is obtained which is dissolved and subjected to column chromatography (silica gel, dichloromethane:acetonitrile=3:1). (2-{2-[(4'-Octyloxy-biphenyl-4-carbonyl)-amino]-phenyl}-ethyl)-phosphonic acid diethyl ester is obtained in the form of a colourless solid.

PREPARATION EXAMPLE 14

{2-[(4'-Octyloxy-biphenyl-4-carbonyl)-amino]-phenyl}-phosphonic acid diethyl ester (Compound of Example 20 in TABLE 1 Below)

At rt, to a solution of (2-Amino-phenyl)-phosphonic acid diethyl ester in EtOAc are added 10 equivaltents of pyridine followed by 1 equivalent of 4'-octyloxy-biphenyl-4-carbonylchloride (VAW132) and the mixture obtained is stirred for ca. 25 minutes. The mixture obtained is subjected to an aqueous work-up ($NaHCO_3$/EtOAc), the organic phase obtained is dried, solvent is evaporated and the evaporation residue is subjected to column chromatography. {2-[(4'-Octyloxy-biphenyl-4-carbonyl)-amino]-phenyl}-phosphonic acid diethyl ester is obtained.

PREPARATION OF INTERMEDIATES

Preparation Example A

[Difluoro-(2-nitro-phenyl)-methyl]-phosphonic acid diethyl ester and 1,1,2,2-tetrafluoro-2-(2-nitro-phenyl)-ethyl]-phosphonic acid diethyl ester Compounds of formula

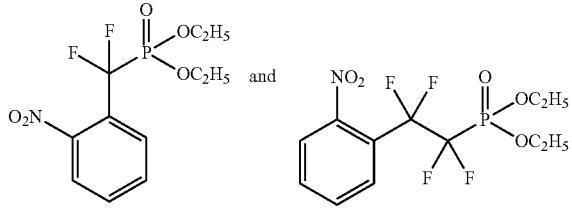

To a suspension of 8.5 g Zn powder in 50 ml of DMF are added 5 g diethyl, (bromodifluoromethyl)-phosphonate followed by aprox. 0.4 ml of trimethylsilylchloride (activation of zinc). An exothermic reaction occurs and to the mixture additional 27 g diethyl, (bromodifluoromethyl)-phosphonate are added in such a rate that the temperature is kept below 50° C. To the mixture obtained, after one hour at rt, 18 g of Cu(I)Br are added in one portion. To the mixture obtained, after one hour at rt, 14.9 g of 1-iodo-2-nitrobenzene, dissolved in DMF, are added in such a rate that 40° C. are not exceeded. The suspension obtained is allowed to stir for 15 hours at rt. The mixture obtained is partitioned between water and TBME. The aqueous phase obtained is extracted with TBME and the combined organic phases are dried. From the mixture obtained solvent is evaporated and a brownish oil is obtained which is subjected to column chromatography (silica gel, toluene:ethylacetate=3.2 to 1:1) [Difluoro-(2-nitro-phenyl)-methyl]-phosphonic acid diethyl ester (MS $MNa^+$ 332) and 1,1,2,2-tetrafluoro-2-(2-nitro-phenyl)-ethyl]-phosphonic acid diethyl ester (MS $MNa^+$ 382) are obtained in the form of yellow oils.

Analogously to the method as described in preparation example 1, but using 1-iodo-3-nitrobenzene instead of of 1-iodo-2-nitro-benzene as a starting material the compounds difluoro-(3-nitro-phenyl)-methyl]-phosphonic acid diethyl ester (MS $MNa^+$ 332) and [1,1,2,2-tetrafluoro-2-(3-nitro-phenyl)-ethyl]-phosphonic acid diethyl ester (MS $MNa^+$ 382) are obtained.

Analogously to the method as described in preparation example 1, but using 1-iodo-4-nitrobenzene instead of of 1-iodo-2-nitro-benzene as a starting material the compounds [difluoro-(4-nitro-phenyl)-methyl]-phosphonic acid diethyl ester (MS $MNa^+$ 332) and [1,1,2,2-Tetrafluoro-2-(4-nitro-phenyl)-ethyl]-phosphonic acid diethyl ester (MS $MNa^+$ 382) are obtained

Preparation Example B

[(2-Aminophenyl)-difluoro-methyl]-phosphonic acid diethyl ester NVP-VAV664

Compound of Formula

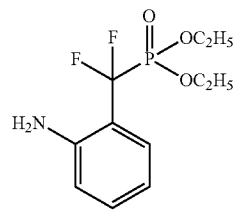

A solution of difluoro-(3-nitro-phenyl)-methyl]-phosphonic acid diethyl ester in EtOH is hydrogenated over 10 w/w % palladium on charcoal. From the mixture obtained after hadrogenation Pd/C is filtered of, solvent is evaporated and the evaporation residue obtained is subjected to column chromatography. [(2-Amino-phenyl)-difluoro-methyl]-phosphonic acid diethyl ester is obtained in the form of a colourless oil. MS MNa$^+$ 302.

Analogously to the method as described in preparation example B, the following compounds are obtained:

[(2-Ethylamino-phenyl)-difluoro-methyl]-phosphonic acid diethyl ester, such as of formula

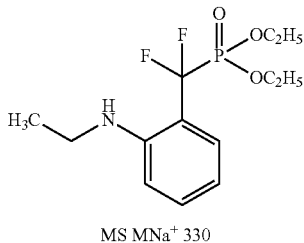

MS MNa$^+$ 330

[Difluoro-(2-hydroxyamino-phenyl)-methyl]-phosphonic acid diethyl ester, such as of formula

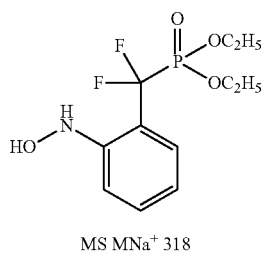

MS MNa$^+$ 318

[(3-Amino-phenyl)-difluoro-methyl]-phosphonic acid diethyl ester, such as of formula

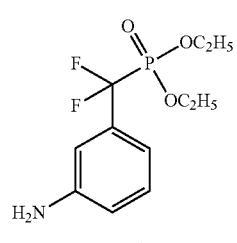

MS MNa$^+$ 302

[(3-Ethylamino-phenyl)-difluoro-methyl]-phosphonic acid diethyl ester, such as of formula

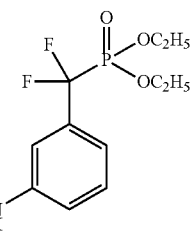

MS MNa$^+$ 330

[2-(3-Amino-phenyl)-1,1,2,2-tetrafluoro-ethyl]-phosphonic acid diethyl ester, such as of formula

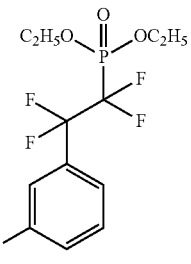

MS MNa$^+$ 352 and
[2-(3-Ethylamino-phenyl)-1,1,2,2-tetrafluoro-ethyl]-phosphonic acid diethyl ester, such as of formula

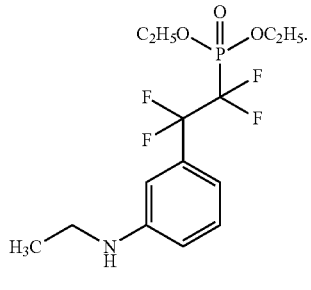

MS MNa$^+$ 380

Preparation Example C

Ethynyl-phosphonic acid diethyl ester

A solution of 50 ml of 0.5 M ethynyl-magnesiumbromide in THF is added to a cooled solution of phosphorochloridic acid, diethylester in such a rate that the temperature does not exceed 8° C. The mixute obtained is kept for 30 minutes at 5° C. and is stirred for 2 hours at rt. Following an acidic work-up and subsequent column chromatography (silica gel, toluene:ethylacetate=1:1) ethynyl-phosphonic acid diethyl ester is obtained in the form of an colourless oil. MS: MNa$^+$ 185.

Preparation Example D (2-Nitro-phenylethynyl)-phosphonic acid diethyl ester

To a solution of 300 mg of ethynyl-phosphonic acid diethyl ester, 494 mg of 1-iodo-2-nitrobenzene and 0.28 ml of di-isopropylamine in 15 ml THF are sequentially added 43 mg of bis-(triphenylphosphin)-palladium(II)-dichloride and 12 mg of copper(I)iodide and the mixture obtained is refluxed for approximately 2 hours. Following an acidic work-up (1N aqueous HCl and EtOAc) and subsequent column chromatography (2-nitro-phenylethynyl)-phosphonic acid diethyl ester is obtained in the form of a slightly brownish oil.

Analogously to the method as described in preparation example D, but using 1-iodo-3-nitrobenzene instead of 1-iodo-2-nitrobenzene the compound (3-nitro-phenylethynyl)-phosphonic acid diethyl ester of formula

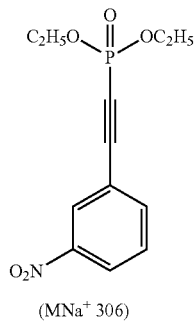

(MNa+ 306)

Preparation Example E

4'-Octyloxy-biphenyl-4-carbonyl chloride 20 g of 4'-octyloxy-biphenyl-4-carboxylic acid are suspended in 140 ml of $CH_2Cl_2$ and to the suspension obtained 23 ml of thionylchloride and a catalytic amount of DMF are added. The mixture obtained is allowed to stir at rt for 21 hours. A clear solution is obtained which is diluted with 50 ml of toluene and the diluted mixture is concentrated at reduced pressure. The concentrated solution solution obtained (aproximately 50 ml) is again diluted with 50 ml of toluene and evaporated to dryness. 4'-Octyloxy-biphenyl-4-carbonyl chloride is obtained in crystalline form.

Preparation Example F (2-Nitro-phenyl)-phosphonic acid diethyl ester 3.9 g of Cu(II) acetate are added to a solution of 5 g 1-iodo-2-nitrobenzene and 5 g of triethylphosphite in 20 ml of EtOH, the mixture obtained is refluxed for 24 hours, cooled to rt and partitioned between EtOAc and half-saturated aqueous NaCl-solution. The organic layer obtained is dried, solvent is evaporeated and the evaporation residue is subjected to column chromatography (silicagel, toluene:acetonitrile=3:1). (2-Nitro-phenyl)-phosphonic acid diethyl ester is obtained in the form of an orange oil. MS: MNa+ 282

Preparation Example G (2-Amino-phenyl)-phosphonic acid diethyl ester

A solution of (2-nitro-phenyl)-phosphonic acid diethyl ester in methanol (is hydrogenated over 10 w/w % palladium on charcoal. From the mixure obtained Pd/C is filtrated off, solvent from the filtrate obtained is evaporated and the evaporation residue is subjected to column chromatography. (2-Amino-phenyl)-phosphonic acid diethyl ester is obtained in the form of a colourless oil. MS: MNa+ 252

Analogously to methods as described in previous preparation examples, but using appropriate starting materials (intermediates) compounds of formula

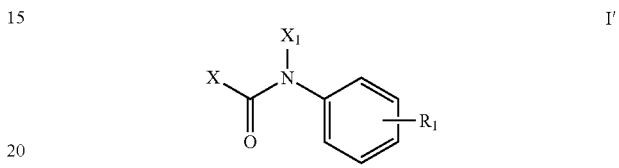

I' wherein $R_1$ and X are as set out in TABLE I below, having the characterization DATA as defined in TABLE 1 below under "DATA", are obtained. The characterization data in TABLE 1 is $^1$HNMR data or mass spectroscopy data (MS).

In compounds of examples 1 to 37, 39, 40, 42, 43, 45 and 46 to 52 $X_1$ is hydrogen; in examples 38, 41 and 44 $X_1$ is a group of formula

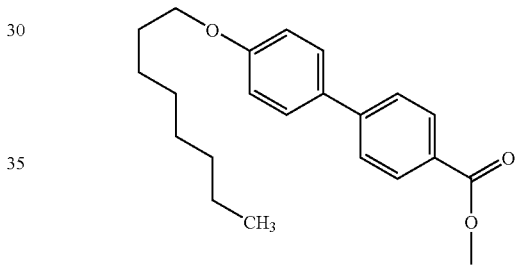

In the compound of examples 2 to 6, 9, 12, 18 to 20, 29 to 32, 34 to 37, 39, 40, 42, 46, 47 and 49 $R_1$ is attached in position 2 of the phenyl ring.

In the compound of examples 1, 7, 10, 13, 21 to 24, 27, 28, 43, 45, 48, 50 and 53 $R_1$ is attached in position 3 of the phenyl ring.

In the compound of examples 8, 11, 14 to 17, 25, 26, 33, 38, 41, 44, 48a, 51 and 52 $R_1$ is attached in position 4 of the phenyl ring.

TABLE 1

| EX | X | $R_1$ | DATA<br>$^1$HNMR or MS |
|---|---|---|---|
| 1 | ![structure] | ![structure] | CDCl3/DMSO, 9.47 (s, 1H, NH), 7.95 (d, J = 8 Hz, 2H), 7.73 (s, 1H), 7.59 (d, J = 8 Hz, 2H), 7.50 (d, J = 8 Hz, 2H), 7.29 (t, J = 8 Hz, 1H), 6.97 (dd, 1H) 6.86 (d, J = 8 Hz, 2H), 4.41 (s, 2H), 3.94 (m, 2H), 1.74 (m, 2H), 0.82 (m, 3H) |

TABLE 1-continued

| EX | X | R₁ | DATA ¹HNMR or MS |
|---|---|---|---|
| 2 | 4'-methyl-4-(heptyloxy)biphenyl (with CH₃ chain) | ethylphosphonic acid (HO-P(O)(OH)-CH₂CH₃) | CDCl3, 9.95 (s, 1H, NH), 8.09 (d, J = 8 Hz, 2H), 7.84 (d, J = 7.5 Hz, 1H). 7.63 (d, J = 8 Hz, 2H), 7.53 (d, J = 8,5 Hz, 2H), 7.28 (m, 1H), 7.21 (d, J = 7 Hz, 1H), 7.09 (t, J = 7.5 Hz, 1H), 6.97 (d, J = 8,5 Hz, 2H), 3.99 (t, J = 6,5 Hz, 2H), 3.14 (d, J = 21 Hz, 2H), 1.81 (m, J = 7,5 Hz, 2H), 1.47 (m, J = 7 Hz, 2H), 1.32 (m, 8H). 0.89 (t, J = 6.5 Hz, 3H) |
| 3 | 4'-methyl-4-hexylbiphenyl | ethylphosphonic acid | MeOD, 8.20, 8.18, 7.76, 7.74, 7.61, 7.59, 7.29, 7.27, 7.25, 7.24, 7.22, 7.15, 7.13, 7.12, 3.08, 3.03, 2.68, 2.66, 2.64, 1.69, 1.67, 1.66, 1.64, 1.62, 1.34, 0.92, 0.90, 0.88 |
| 4 | 1-phenyl-3-adamantyl | ethylphosphonic acid | MeOD, 7.97, 7.48, 7.46, 7.43, 7.32, 7.30, 7.28, 7.19, 7.17, 7.15, 7.13, 3.13, 3.08, 2.99, 2.86, 2.69. 2.15, 2.08, 1.97. |
| 5 | 4'-methyl-4-methoxybiphenyl | ethylphosphonic acid | M − H 396 |
| 6 | 4'-methyl-4-(heptyloxy)biphenyl | 1,1-difluoroethylphosphonic acid | MNa₂ − H⁺ 576, MNa⁺ 554 |
| 7 | 4'-methyl-4-(heptyloxy)biphenyl | 1,1-difluoroethylphosphonic acid | MNa₂ — H⁺ 576 |

TABLE 1-continued
| EX | X | R₁ | DATA ¹HNMR or MS |
|---|---|---|---|
| 8 | 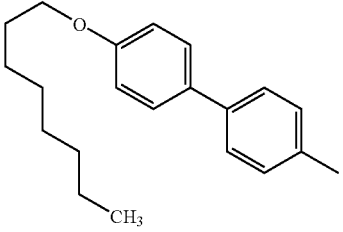 | 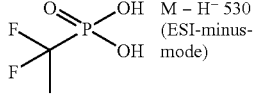 | M − H⁻ 530 (ESI-minus-mode) |
| 9 | 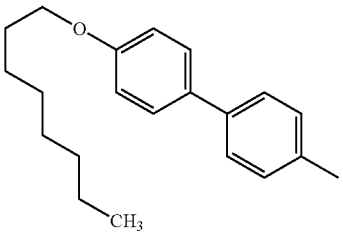 | 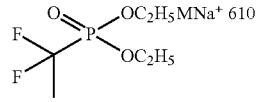 | MNa⁺ 610 |
| 10 | 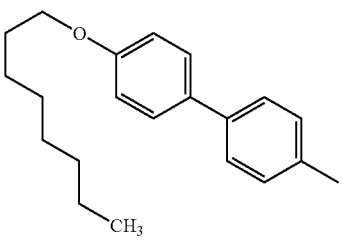 | 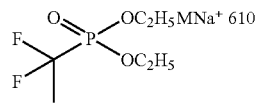 | MNa⁺ 610 |
| 11 | 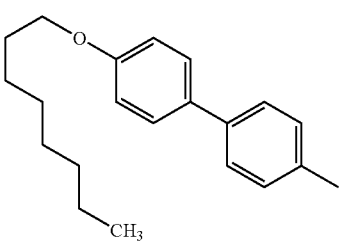 | 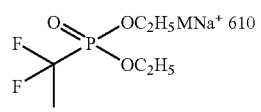 | MNa⁺ 610 |
| 12 | 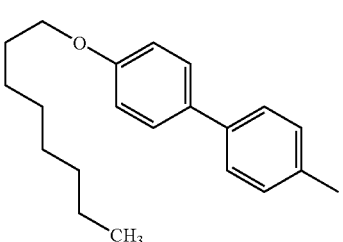 | 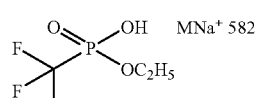 | MNa⁺ 582 |
| 13 | 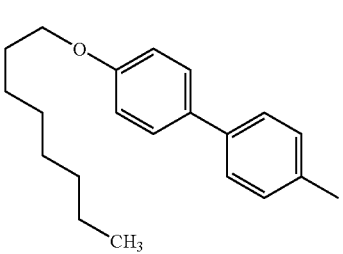 | 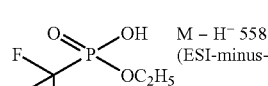 | M − H⁻ 558; (ESI-minus-mode) |

TABLE 1-continued

| EX | X | R₁ | DATA ¹HNMR or MS |
|---|---|---|---|
| 14 | 4-heptyloxy-4'-methylbiphenyl (with CH₃ branch) | P(=O)(OH)(OC₂H₅)–CF₂– | MNa⁺ 604 |
| 15 | 4-heptyloxy-4'-methylbiphenyl (with CH₃ branch) | (C₂H₅O)₂P(=O)–C(CF₃)F₂ | MNa⁺ 660 |
| 16 | 4-heptyloxy-4'-methylbiphenyl (with CH₃ branch) | C₂H₅O–P(=O)(OH)–C(CF₃)F₂ | MNa⁺ 632 |
| 17 | 4-heptyloxy-4'-methylbiphenyl (with CH₃ branch) | HO–P(=O)(OH)–C(CF₃)F₂ | MNa⁺ 626 |
| 18 | 4-heptyloxy-4'-methylbiphenyl (with CH₃ branch) | HO–P(=O)(OH)–CH₃ | MNa⁺ 504 |
| 19 | 4-heptyloxy-4'-methylbiphenyl (with CH₃ branch) | HO–P(=O)(OC₂H₅)–CH₃ | MNa⁺ 532 |

TABLE 1-continued

| EX | X | R₁ | DATA ¹HNMR or MS |
|---|---|---|---|
| 20 | 4'-methylbiphenyl-4-yl O-CH₂-(hexyl with CH₃ branch) | $C_2H_5O-P(=O)(OC_2H_5)(CH_3)$ | MNa⁺ 560 |
| 21 | 4'-methylbiphenyl-4-yl O-CH₂-(hexyl with CH₃ branch) | $HO-P(=O)(OH)(CH_3)$ | MNa⁺ 504 |
| 22 | 4'-methylbiphenyl-4-yl O-CH₂-(hexyl with CH₃ branch) | $HO-P(=O)(OC_2H_5)(CH_3)$ | MNa⁺ 532 |
| 23 | 4'-methylbiphenyl-4-yl O-CH₂-(heptyl with CH₃ branch) | $C_2H_5O-P(=O)(OC_2H_5)(CH_3)$ | MNa⁺ 560 |
| 24 | 4'-methylbiphenyl-4-yl O-CH₂-(heptyl with CH₃ branch) | $HO-P(=O)(OH)(CH_3)$ | MNa⁺ 504 |
| 25 | 4'-methylbiphenyl-4-yl O-CH₂-(heptyl with CH₃ branch) | $HO-P(=O)(OC_2H_5)(CH_3)$ | MNa⁺ 532 |

TABLE 1-continued

| EX | X | R₁ | DATA ¹HNMR or MS |
|----|---|-----|------------------|
| 26 | 4'-methyl-4-(heptyloxy)biphenyl | (H₅C₂O)(OC₂H₅)P(=O)CH₃ | MNa⁺ 560 |
| 27 | 4'-methyl-4-(heptyloxy)biphenyl | (HO)(OH)P(=O)C₂H₅ | MNa⁺ 494 |
| 28 | 4'-methyl-4-(heptyloxy)biphenyl | (O=)(OH)(OC₂H₅)P–C₂H₅ | MNa⁺ 522 |
| 29 | 4'-methyl-4-(nonyloxy)biphenyl | (C₂H₅O)(OC₂H₅)P(=O)CH₃ | M − H 578.3 |
| 30 | 4'-methyl-4-(nonyloxy)biphenyl | (HO)(OH)P(=O)C₂H₅ | M − H 522.2 |

TABLE 1-continued

| EX | X | R₁ | DATA ¹HNMR or MS |
|---|---|---|---|
| 31 | 4-(benzyloxy)-4'-methylbiphenyl group | ethylphosphonic acid | M − H 472.2 |
| 32 | 4'-hydroxy-4-methylbiphenyl group | ethylphosphonic acid | M − H 382.2 |
| 33 | 4-(heptyloxy)-4'-methylbiphenyl group | ethylphosphonic acid | M − H 494.3 |
| 34 | 4-methylbiphenyl group | ethylphosphonic acid | M − H 366.1 |
| 35 | 4-(butoxy)-4'-methylbiphenyl group | ethylphosphonic acid | M − H 438.2 |
| 36 | 4-hexyl-4'-methylbiphenyl group | ethylphosphonate choline ester | M − H 537.4 |

TABLE 1-continued

| EX | X | R₁ | DATA ¹HNMR or MS |
|---|---|---|---|
| 37 | 4'-methyl-4-(heptyloxy)biphenyl | F,F-difluoro(methyl)(ethoxy)(methoxy)phosphonate | MNa⁺ 596 |
| 38 | 4'-methyl-4-(heptyloxy)biphenyl | pentafluoro diethyl phosphonate | MNa⁺ 984 |
| 39 | 4'-methyl-4-(heptyloxy)biphenyl | (pivaloyloxymethyl) methyl phosphonate (mono) | M − H 608.2<br>M − H 610.4 |
| 40 | 4'-methyl-4-(heptyloxy)biphenyl | bis(pivaloyloxymethyl) methyl phosphonate | MNa⁺ 746.2<br>M2Na⁺ 1469.5 |
| 41 | 4'-methyl-4-(heptyloxy)biphenyl | difluoro(methyl) diethyl phosphonate | MNa⁺ 934 |

TABLE 1-continued
| EX | X | R₁ | DATA ¹HNMR or MS |
|----|---|-----|------------------|
| 42 | 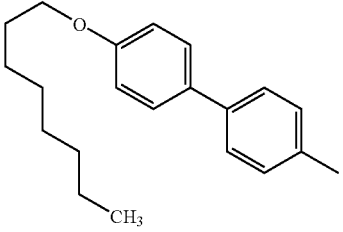 | 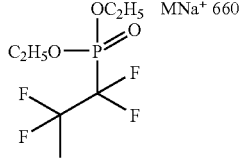 | MNa⁺ 660 |
| 43 | 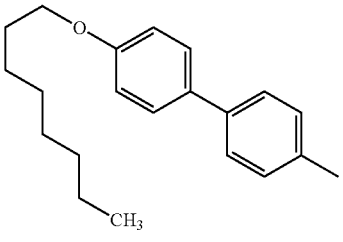 | 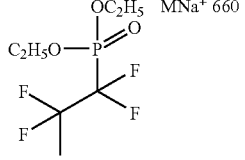 | MNa⁺ 660 |
| 44 | 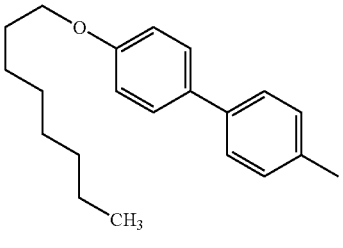 | 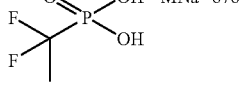 | MNa⁺ 878 |
| 45 | 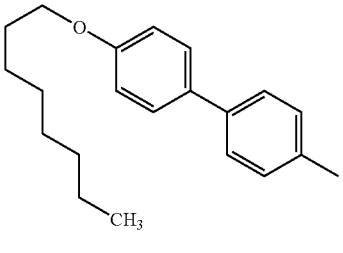 | 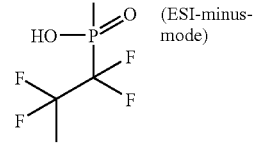 | M − H⁻ 580 (ESI-minus-mode) |
| 46 | 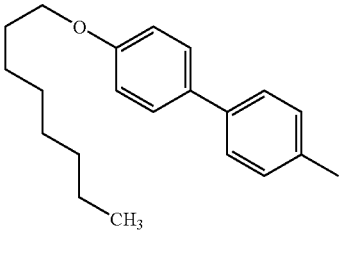 | 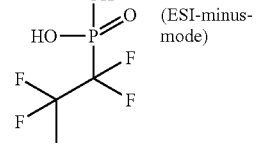 | M − H⁻ 580 (ESI-minus-mode) |
| 47 | 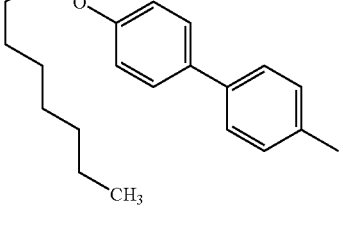 | 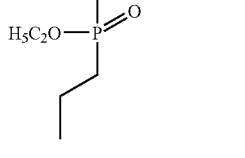 | MNa⁺ 588 |

TABLE 1-continued

| EX | X | R₁ | DATA ¹HNMR or MS |
|---|---|---|---|
| 48 | (4'-methylbiphenyl-4-yl)oxy with heptyl chain | P(=O)(OC₂H₅)(OC₂H₅)-propyl | MNa⁺ 588 |
| 48a | (4'-methylbiphenyl-4-yl)oxy with heptyl chain | P(=O)(OC₂H₅)(OC₂H₅)-propyl | MNa⁺ 588 |
| 49 | (4'-methylbiphenyl-4-yl)oxy with heptyl chain | P(=O)(OH)(OH)-propyl | M − H⁻ 508 (ESI-minus-mode) |
| 50 | (4'-methylbiphenyl-4-yl)oxy with heptyl chain | P(=O)(OH)(OH)-propyl | M − H⁻ 508 (ESI-minus-mode) |
| 51 | (4'-methylbiphenyl-4-yl)oxy with heptyl chain | P(=O)(OH)(OH)-propyl | M − H⁻ 508 (ESI-minus-mode) |
| 52 | (4'-methylbiphenyl-4-yl)oxy with heptyl chain | P(=O)(OH)(OH)-methyl | M − H⁻ 480 (ESI-minus-mode) |

TABLE 1-continued

| EX | X | R₁ | DATA ¹HNMR or MS |
|---|---|---|---|
| 53 | (long chain–O–biphenyl–CH₃ structure with CH₃ terminus) | –P(=O)(OC₂H₅)(OC₂H₅) with ethyl | MNa⁺ 574 |

The compound structure of the compounds of EX 1 to 53 in TABLE 1 is also confirmed by ¹H-NMR and/or ¹³C-NMR data.

Analogously to the methods as described in previous preparation examples, but using appropriate starting materials (intermediates) compounds of formula

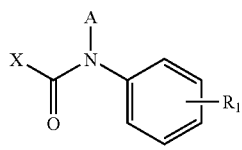

I wherein R₁ and X are as set out in TABLE 2 below, having the characterization DATA as defined in TABLE 2 below under "DATA", are obtained. The characterization data in TABLE 2 is mass spectroscopy data (MS).

A is ethyl in the compound of example 54 and methyl in all other compounds of TABLE 2.

R₁ is in position 2 of the phenyl ring in examples 55, 56 and 63.

R₁ is in position 3 of the phenyl ring in examples 54, 59 to 61 and 64.

R₁ is in position 4 of the phenyl ring in examples 57, 58 and 62.

TABLE 2

| EX | X | R₁ | DATA (MS) |
|---|---|---|---|
| 54 | (chain–O–biphenyl–CH₃) | –P(=O)(OC₂H₅)(OC₂H₅)CF₂– | MNa⁺ 638 |
| 55 | (chain–O–biphenyl–CH₃) | –P(=O)(OC₂H₅)(OC₂H₅)CF₂– | MNa⁺ 624 |
| 56 | (chain–O–biphenyl–CH₃) | –P(=O)(OCH₃)(OC₂H₅)CF₂– | MNa⁺ 610 |

TABLE 2-continued

| EX | X | R₁ | DATA (MS) |
|---|---|---|---|
| 57 | 4'-methyl-biphenyl-4-yl O-heptyl ether (with CH₃ branch) | $CF_2P(O)(OC_2H_5)_2$ | MNa⁺ 624 |
| 58 | 4'-methyl-biphenyl-4-yl O-heptyl ether (with CH₃ branch) | $CF_2P(O)(OCH_3)(OC_2H_5)$ | MNa⁺ 610 |
| 59 | 4'-methyl-biphenyl-4-yl O-heptyl ether (with CH₃ branch) | $CF_2P(O)(OC_2H_5)_2$ | MNa⁺ 624 |
| 60 | 4'-methyl-biphenyl-4-yl O-heptyl ether (with CH₃ branch) | $CF_2P(O)(OCH_3)(OC_2H_5)$ | MNa⁺ 610 |
| 61 | 4'-methyl-biphenyl-4-yl O-heptyl ether (with CH₃ branch) | $CF_2P(O)(OH)(OC_2H_5)$ | MNa⁺ 596 |
| 62 | 4'-methyl-biphenyl-4-yl O-heptyl ether (with CH₃ branch) | $CF_2P(O)(OH)_2$ | MNa⁺ 568 |

TABLE 2-continued

| EX | X | R₁ | DATA (MS) |
|---|---|---|---|
| 63 | 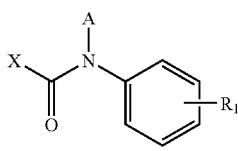 | 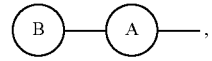 | MNa⁺ 568 |
| 64 |  | 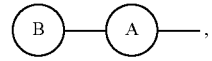 | MNa⁺ 568 |

The compound structure of the compounds of EX 54 to 64 in TABLE 2 is also confirmed by $^1$H-NMR and/or $^{13}$C-NMR data.

The invention claimed is:
1. A compound of formula

$$I$$

wherein
A is hydrogen or $(C_{1-4})$alkyl,
R₁ is a group Y—R₂,
Y is not present or is $(C_{1-4})$alkylene, which alkylene is optionally substituted with halogen,
R₂ is —P(O)(OH)(OH),
X is a group of formula ring A is phenylene, and
ring B is phenyl optionally substituted with R₅, wherein
R₅ is halogen, halo($C_{1-4}$)alkyl, halo($C_{1-4}$)alkyloxy, carboxyl, nitro, amino, a phosphor containing group, a sulfur containing group, or acyl or acyloxy comprising 1 to 12 carbon atoms beside the CO group, or
R₅ is a group —ZR₆, wherein
Z is not present or is NH, O or S, and
R₆ is hydrogen if Z is present, or
R₆ is $(C_{3-12})$cycloalkyl, $(C_{5-12})$cycloalkenyl, $(C_{6-12})$ aryl, aromatic or aliphatic heterocyclyl, comprising 3 to 12 ring members and 1 to 4 heteroatoms selected from N, O or S, or $(C_{1-22})$alkyl, $(C_{2-22})$alkenyl, or $(C_{2-22})$alkynyl, which alkyl, alkenyl or alkynyl can be unsubstituted or substituted with $(C_{6-12})$aryl, or
a prodrug of a compound of formula I which is a compound of formula I wherein R₂ is a phosphoric acid ester or phosphoric acid amide group, optionally in salt form, wherein the phosphoric acid ester or amide moiety is a group which is hydrolysable, or
a prodrug of a compound of formula I which is a compound of formula I wherein the nitrogen of the amide group is substituted with a group which is hydrolysable.

2. The compound of formula I according to claim 1, wherein
A is hydrogen, methyl or ethyl,
R₁ is a group Y—R₂,
Y is not present or is —CH₂—, —CF₂— or —CF₂—CF₂—,
R₂ is —P(O)(OH)(OH);
X is a group of formula ring A is unsubstituted phenylene, and
ring B is phenyl, which phenyl is unsubstituted or substituted with hexyl, hydroxy, methoxy, butoxy, octyloxy, decyloxy or benzyloxy.

3. The compound of formula I according to claim 1, wherein A is hydrogen.

4. The compound of formula I according to claim 1; wherein A is $(C_{1-4})$alkyl.

5. The compound according to claim 1, selected from the group consisting of
4'-Octyloxy-biphenyl-4-carboxylic acid [3-(1,1,4-trioxo-[1,2,5]thiadiazolidin-2-yl)-phenyl]-amide,
{2-[(4'-Octyloxy-biphenyl-4-carbonyl)-amino]-benzyl}-phosphonic acid,
{2-[(4'-Hexyl-biphenyl-4-carbonyl)-amino]-benzyl}-phosphonic acid, {2-[(4'-Methoxy-biphenyl-4-carbonyl)-amino]-benzyl}-phosphonic acid,
(Difluoro-{2-[(4'-octyloxy-biphenyl-4-carbonyl)-amino]-phenyl}-methyl)-phosphonic acid,
(Difluoro-{3-[(4'-octyloxy-biphenyl-4-carbonyl)-amino]-phenyl}-methyl)-phosphonic acid,
(Difluoro-{4-[(4'-octyloxy-biphenyl-4-carbonyl)-amino]-phenyl}-methyl)-phosphonic acid,
(Difluoro-{2-[(4'-octyloxy-biphenyl-4-carbonyl)-amino]-phenyl}-methyl)-phosphonic acid diethyl ester,
(Difluoro-{3-[(4'-octyloxy-biphenyl-4-carbonyl)-amino]-phenyl}-methyl)-phosphonic acid diethyl ester,
(Difluoro-{4-[(4'-octyloxy-biphenyl-4-carbonyl)-amino]-phenyl}-methyl)-phosphonic acid diethyl ester,
(Difluoro-{2-[(4'-octyloxy-biphenyl-4-carbonyl)-amino]-phenyl}-methyl)-phosphonic acid monoethyl ester,
(Difluoro-{3-[(4'-octyloxy-biphenyl-4-carbonyl)-amino]-phenyl}-methyl)-phosphonic acid monoethyl ester,
(Difluoro-{4-[(4'-octyloxy-biphenyl-4-carbonyl)-amino]-phenyl}-methyl)-phosphonic acid monoethyl ester,
(1,1,2,2-Tetrafluoro-2-{4-[(4'-octyloxy-biphenyl-4-carbonyl)-amino]-phenyl}-ethyl)-phosphonic acid diethyl ester,
(1,1,2,2-Tetrafluoro-2-{4-[(4'-octyloxy-biphenyl-4-carbonyl)-amino]-phenyl}-ethyl)-phosphonic acid monoethyl ester,
(1,1,2,2-Tetrafluoro-2-{4-[(4'-octyloxy-biphenyl-4-carbonyl)-amino]-phenyl}-ethyl)-phosphonic acid,
{2-[(4'-Octyloxy-biphenyl-4-carbonyl)-amino]-phenyl}-phosphonic acid,
{2-[(4'-Octyloxy-biphenyl-4-carbonyl)-amino]-phenyl}-phosphonic acid monoethyl ester,
{2-[(4'-Octyloxy-biphenyl-4-carbonyl)-amino]-phenyl}-phosphonic acid diethyl ester,
{3-[(4'-Octyloxy-biphenyl-4-carbonyl)-amino]-phenyl}-phosphonic acid,
{3-[(4'-Octyloxy-biphenyl-4-carbonyl)-amino]-phenyl}-phosphonic acid monoethyl ester,
{3-[(4'-Octyloxy-biphenyl-4-carbonyl)-amino]-phenyl}-phosphonic acid diethyl ester,
{4-[(4'-Octyloxy-biphenyl-4-carbonyl)-amino]-phenyl}-phosphonic acid monoethyl ester,
{4-[(4'-Octyloxy-biphenyl-4-carbonyl)-amino]-phenyl}-phosphonic acid diethyl ester,
3-[(4'-Octyloxy-biphenyl-4-carbonyl)-amino]-benzyl}-phosphonic acid,
{3-[(4'-Octyloxy-biphenyl-4-carbonyl)-amino]-benzyl}-phosphonic acid monoethyl ester,
{2-[(4'-Decyloxy-biphenyl-4-carbonyl)-amino]-benzyl}-phosphonic acid diethyl ester,
{2-[(4'-Decyloxy-biphenyl-4-carbonyl)-amino]-benzyl}-phosphonic acid,
{2-[(4'-Benzyloxy-biphenyl-4-carbonyl)-amino]-benzyl}-phosphonic acid,
{2-[(4'-Hydroxy-biphenyl-4-carbonyl)-amino]benzyl}-phosphonic acid,
{4-[(4'-Octyloxy-biphenyl-4-carbonyl)-amino]-benzyl}-phosphonic acid,
{2-[(Biphenyl-4-carbonyl)-amino]benzyl}-phosphonic acid,
{2-[(4'-Butoxy-biphenyl-4-carbonyl)-amino]-benzyl}-phosphonic acid,
[2-({2-[(4'-Hexyl-biphenyl-4-carbonyl)-amino]benzyl}-hydroxy-phosphinoyloxy)-ethyl]-trimethyl-ammonium,
(Difluoro-{2-[(4'-octyloxy-biphenyl-4-carbonyl)-amino]-phenyl}-methyl)-phosphonic acid ethyl ester methyl ester,
2,2-Dimethyl-propionic acid hydroxy-{2-[(4'-octyloxy-biphenyl-4-carbonyl)-amino]-benzyl}-phosphinoyloxymethyl ester,
2,2-Dimethyl-propionic acid (2,2-dimethyl-propionyloxymethoxy)-{2-[(4'-octyloxy-biphenyl-4-carbonyl)-amino]-benzyl}-phosphinoyloxymethyl ester,
(1,1,2,2-Tetrafluoro-2-{2-[(4'-octyloxy-biphenyl-4-carbonyl)-amino]-phenyl}-ethyl)-phosphonic acid diethyl ester,
(1,1,2,2-Tetrafluoro-2-{3-[(4'-octyloxy-biphenyl-4-carbonyl)-amino]-phenyl}-ethyl)-phosphonic acid diethyl ester,
(1,1,2,2-Tetrafluoro-2-{3-[(4'-octyloxy-biphenyl-4-carbonyl)-amino]-phenyl}-ethyl)-phosphonic acid,
(1,1,2,2-Tetrafluoro-2-{2-[(4'-octyloxy-biphenyl-4-carbonyl)-amino]-phenyl}-ethyl)-phosphonic acid
(2-{2-[(4'-Octyloxy-biphenyl-4-carbonyl)-amino]-phenyl}-ethyl)-phosphonic acid diethyl ester,
(2-{3-[(4'-Octyloxy-biphenyl-4-carbonyl)-amino]-phenyl}-ethyl)-phosphonic acid diethyl ester,
(2-{4-[(4'-Octyloxy-biphenyl-4-carbonyl)-amino]-phenyl}-ethyl)-phosphoic acid diethyl ester,
(2-{2-[(4'-Octyloxy-biphenyl-4-carbonyl)-amino]-phenyl}-ethyl)-phosphonic acid,
(2-{3-[(4'-Octyloxy-biphenyl-4-carbonyl)-amino]-phenyl}-ethyl)-phosphonic acid,
(2-{4-[(4'-Octyloxy-biphenyl-4-carbonyl)-amino]-phenyl}-ethyl)-phosphonic acid,
{4-[(4'-Octyloxy-biphenyl-4-carbonyl)-amino]-phenyl}-phosphonic acid,
{3-[(4'-Octyloxy-biphenyl-4-carbonyl)-amino]-benzyl}-phosphonic acid diethyl ester,
({2-[Ethyl-(4'-octyloxy-biphenyl-4-carbonyl)-amino]-phenyl}-difluoro-methyl)-phosphonic acid diethyl ester,
(Difluoro-{2-[methyl-(4'-octyloxy-biphenyl-4-carbonyl)-amino]-phenyl}-methyl)-phosphonic acid diethyl ester,
(Difluoro-{2-[methyl-(4'-octyloxy-biphenyl-4-carbonyl)-amino]-phenyl}-methyl)-phosphonic acid ethyl ester methyl ester,
(Difluoro-{4-[methyl-(4'-octyloxy-biphenyl-4-carbonyl)-amino]-phenyl}-methyl)-phosphonic acid diethyl ester,
(Difluoro-{4-[methyl-(4'-octyloxy-biphenyl-4-carbonyl)-amino]-phenyl}-methyl)-phosphonic acid ethyl ester methyl ester,
(Difluoro-{3-[methyl-(4'-octyloxy-biphenyl-4-carbonyl)-amino]-phenyl}-methyl)-phosphonic acid diethyl ester,
-(Difluoro-{3-[methyl-(4'-octyloxy-biphenyl-4-carbonyl)-amino]-phenyl}-methyl)-phosphonic acid ethyl ester methyl ester,
(Difluoro-{3-[methyl-(4'-octyloxy-biphenyl-4-carbonyl)-amino]-phenyl}-methyl)-phosphonic acid monoethyl ester,
(Difluoro-{4-[methyl-(4'-octyloxy-biphenyl-4-carbonyl)-amino]-phenyl}-methyl)-phosphonic acid,
(Difluoro-{2-[methyl-(4'-octyloxy-biphenyl-4-carbonyl)-amino]-phenyl}-methyl)-phosphonic acid, and
(Difluoro-{3-[methyl-(4'-octyloxy-biphenyl-4-carbonyl)-amino]-phenyl}-methyl)-phosphonic acid.

6. The compound according to claim 1 in the form of a salt.
7. A pharmaceutical composition, comprising:
the compound of claim 1 and at least one pharmaceutical excipient.

8. A method of treating cystic fibrosis, comprising:
administering to a subject in need thereof an effective amount of the compound of claim 1.

9. A combination of the compound of claim 1 with at least one second drug substance.

10. A compound of formula

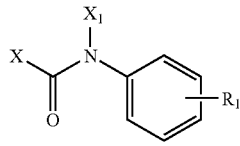

or a salt thereof, wherein $R_1$ is a group $Y-R_2$ or $-Y-R'_2$, Y is not present or is $-CH_2-$, $-CF_2-$ or $-CF_2-CF_2-$, $R_2$ is $-P(O)(OH)(OH)$;

$R'_2$ is $-P(O)(OR_3)(OR_4)$ wherein $R_3$ and $R_4$ independently of each other are hydrogen or $(C_{1-4})$alkyl and wherein at least one of $R_3$ and $R_4$ is $(C_{1-4})$alkyl, or $R'_2$ is $-P(O)(OR'3)(OR'4)$ wherein $R'_3$ and $R'_4$ independently of each other are hydrogen or $(C_{1-4})$alkyl, wherein alkyl is substituted with $(C_{1-6})$alkylcarbonyloxy and wherein at least one of $R'_3$ and $R'_4$ is other than hydrogen; or $R'_2$ is $-P(O)(O)(O-CH_2-CH_2-N^+(C(CH_3)_3)$;

X is a group of formula

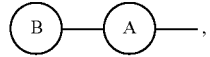

and;

$X_1$ is hydrogen or a group of formula

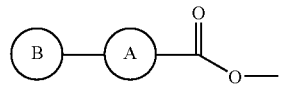

wherein ring A is unsubstituted phenylene, and
ring B is phenyl, which phenyl is unsubstituted or substituted with hexyl, decyl, hydroxy, methoxy, butoxy, n-butoxy, heptyloxy, octyloxy, decyloxy or benzyloxy; and with the proviso that:
either $X_1$ is other than hydrogen, or $R_1$ is $-Y-R'_2$.

11. The compound of claim 10 selected from the group consisting of
(1,1,2,2-Tetrafluoro-2-{4-[(4'-octyloxy-biphenyl-4-carbonyl)-(4'-octyloxy-biphenyl-4-carbonyloxy)-amino]-phenyl}-ethyl)-phosphonic acid diethyl ester,
(Difluoro-{4-[(4'-octyloxy-biphenyl-4-carbonyl)-(4'-octyloxy-biphenyl-4-carbonyloxy)-amino]-phenyl}-methyl)-phosphonic acid diethyl ester, and
(Difluoro-{4-[(4'-octyloxy-biphenyl-4-carbonyl)-(4'-octyloxy-biphenyl-4-carbonyloxy)-amino]-phenyl}-methyl)-phosphonic acid.

12. The compound according to claim 10 in the form of a salt.

13. A pharmaceutical composition, comprising:
the compound of claim 10 and
at least one pharmaceutical excipient.

14. A method of treating cystic fibrosis, comprising:
administering to a subject in need thereof an effective amount of the compound of claim 10.

* * * * *